(12) United States Patent
Gieselman et al.

(10) Patent No.: US 10,002,288 B2
(45) Date of Patent: Jun. 19, 2018

(54) FACIAL IDENTIFICATION TECHNIQUES

(71) Applicant: AWARE, INC., Bedford, MA (US)

(72) Inventors: Neal Joseph Gieselman, Champlin, MN (US); Jonathan Isaac Guillory, Millbury, MA (US)

(73) Assignee: AWARE, INC., Bedford, MA (US)

( * ) Notice: Subject to any disclaimer, the term of this patent is extended or adjusted under 35 U.S.C. 154(b) by 0 days. days.

(21) Appl. No.: 15/838,782

(22) Filed: Dec. 12, 2017

(65) Prior Publication Data

US 2018/0101722 A1 Apr. 12, 2018

Related U.S. Application Data

(63) Continuation of application No. 15/092,328, filed on Apr. 6, 2016, now Pat. No. 9,881,205.

(Continued)

(51) Int. Cl.

| | |
|---|---|
| *G06K 9/00* | (2006.01) |
| *G06K 9/62* | (2006.01) |
| *G06F 9/44* | (2018.01) |
| *A61B 5/1171* | (2016.01) |
| *A61B 5/00* | (2006.01) |

(52) U.S. Cl.
CPC ........ *G06K 9/00295* (2013.01); *A61B 5/1176* (2013.01); *A61B 5/743* (2013.01); *A61B 5/7435* (2013.01); *A61B 5/7485* (2013.01); *G06F 9/4446* (2013.01); *G06F 9/453* (2018.02); *G06K 9/00261* (2013.01); *G06K 9/00281* (2013.01);

(Continued)

(58) Field of Classification Search
USPC ................................................. 382/115–118
See application file for complete search history.

(56) References Cited

U.S. PATENT DOCUMENTS

| | | |
|---|---|---|
| 5,905,807 A | 5/1999 | Kado et al. |
| 8,532,343 B1 | 9/2013 | Freedman |

(Continued)

FOREIGN PATENT DOCUMENTS

| | | |
|---|---|---|
| EP | 1291807 A2 | 3/2003 |
| EP | 2105865 A2 | 9/2009 |
| JP | 2003-141541 A | 5/2003 |

OTHER PUBLICATIONS

FISWG "Facial Image Comparison Feature List for Morphological Analysis" Facial Identification Scientific Working Group; Version 1.0; Aug. 15, 2014.

(Continued)

*Primary Examiner* — Alex Liew
(74) *Attorney, Agent, or Firm* — Jason H. Vick; Sheridan Ross, PC

(57) ABSTRACT

As the use of facial biometrics expands in the commercial and government sectors, the need to ensure that human facial examiners use proper procedures to compare facial imagery will grow. Human examiners have examined fingerprint images for many years such that fingerprint examination processes and techniques have reached a point of general acceptance for both commercial and governmental use. The growing deployment and acceptance of facial recognition can be enhanced and solidified if new methods can be used to assist in ensuring and recording that proper examination processes were performed during the human examination of facial imagery.

30 Claims, 37 Drawing Sheets

Related U.S. Application Data

(60) Provisional application No. 62/168,351, filed on May 29, 2015.

(52) U.S. Cl.
CPC ....... *G06K 9/00288* (2013.01); *G06K 9/6253* (2013.01); *A61B 5/0077* (2013.01)

(56) References Cited

U.S. PATENT DOCUMENTS

| | | |
|---|---|---|
| 2005/0108282 A1* | 5/2005 | Venkatachalam . G06F 17/30277 |
| 2007/0016016 A1 | 1/2007 | Haras et al. |
| 2009/0285456 A1 | 11/2009 | Moon et al. |
| 2010/0066822 A1 | 3/2010 | Steinberg et al. |
| 2010/0104146 A1* | 4/2010 | Momosaki ........ G06F 17/30781 382/118 |
| 2011/0013003 A1 | 1/2011 | Thompson et al. |
| 2013/0044055 A1 | 2/2013 | Karmarkar et al. |
| 2014/0283113 A1 | 9/2014 | Hanna |
| 2015/0124053 A1 | 5/2015 | Tamura et al. |
| 2016/0350586 A1 | 12/2016 | Gieselman et al. |

OTHER PUBLICATIONS

SWGFAST "Document #8—Standard for the Documentation of Analysis, Comparison, Evaluation, and Verification (ACE-V) (Latent)" Scientific Working Group on Friction Ridge Analysis, Study and Technology; Available at http://www.swgfast.org/documents/documentation/121124_Standard-Documentation—ACE-V_2.0.pdf; Sep. 11, 2012.

SWGFAST "Document # 10—Standards for Examining Friction Ridge Impressions and Resulting Conclusions (Latent/Tenprint)" Scientific Working Group on Friction Ridge Analysis, Study and Technology; Available at http://www.swgfast.org/documents/examinations-conclusions/121124_Examinations-Conclusions_2.0.pdf; Sep. 10, 2012.

European Search Report for European Application No. 16020188.5, dated Oct. 26, 2016.

Office Action for U.S. Appl. No. 15/092,328, dated Jun. 15, 2017.

Notice of Allowance for U.S. Appl. No. 15/092,328, dated Nov. 7, 2017.

\* cited by examiner

| Snapshot | Feature | Same/Different | Snapshot Images | Comments | Data Path |
|---|---|---|---|---|---|
| 1 | Forehead | S |  2604 | Forehead Creases | Original:<br>Candidate:<br>Probe:<br>Snapshot: |
| 2 | Ears | S | | Left Ear | |
| 3 | Ears | S | | Right Ear | |
| 4 | Nose | S | | Nose | |
| 5 | Mouth | S | | Mouth | |
| ... | | | | | |

Save    Done

Face/Head Outline
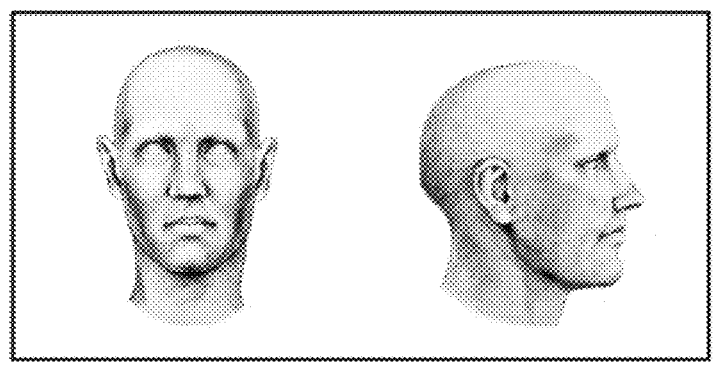
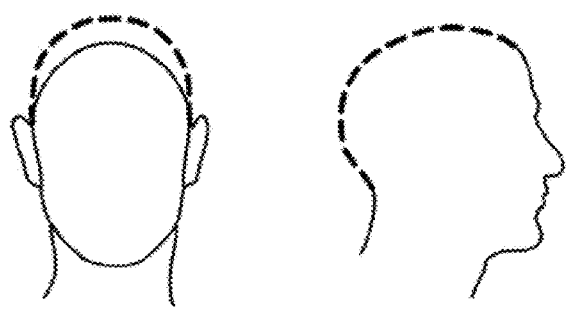
Shape of Cranial Vault
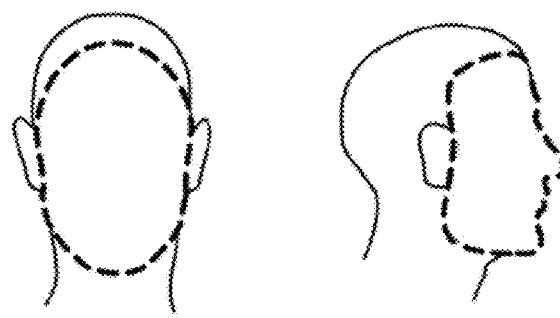
Overall Shape of Face
FIG. 28

Hairline/Baldness Pattern
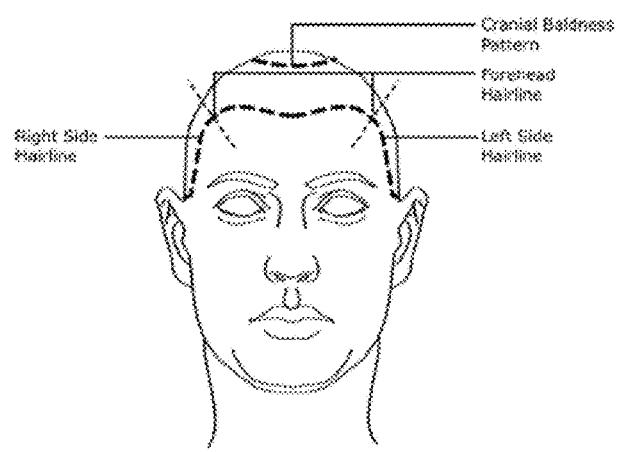
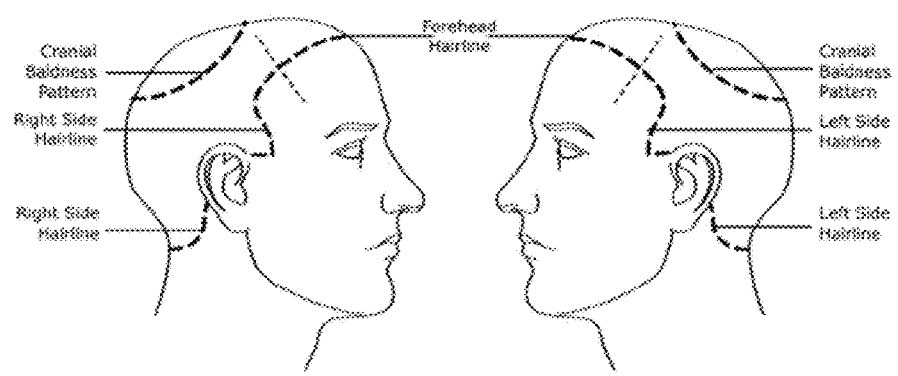
FIG. 29

Forehead (including Brow Ridge)

Nose
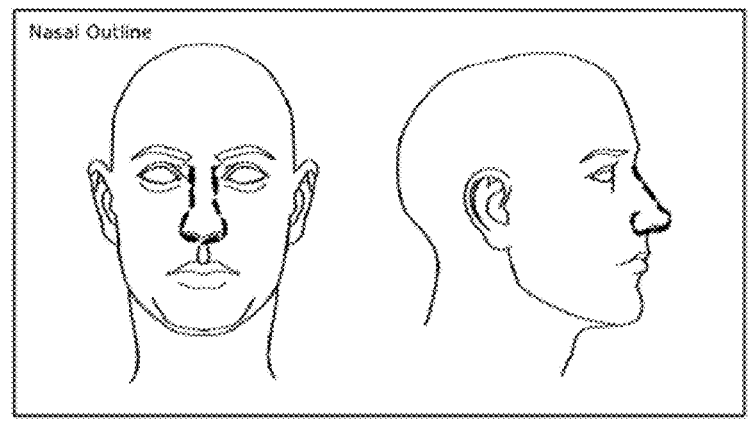
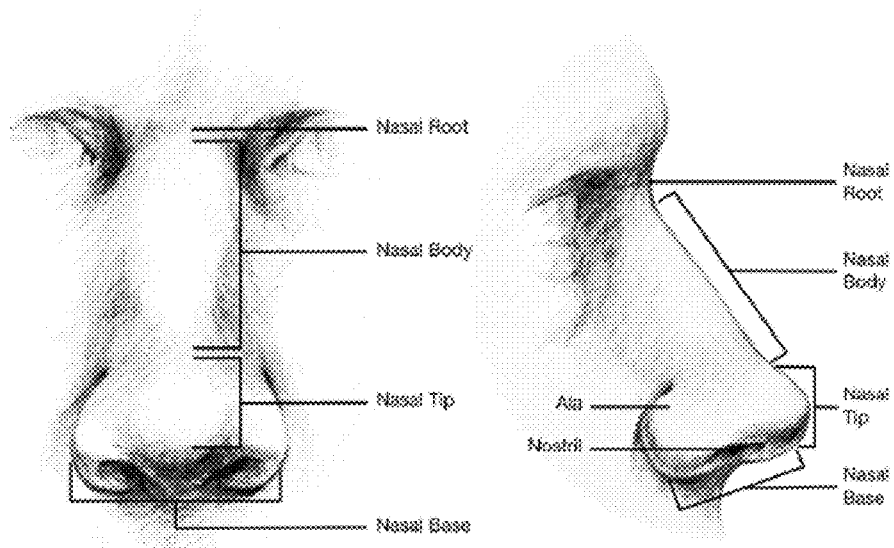
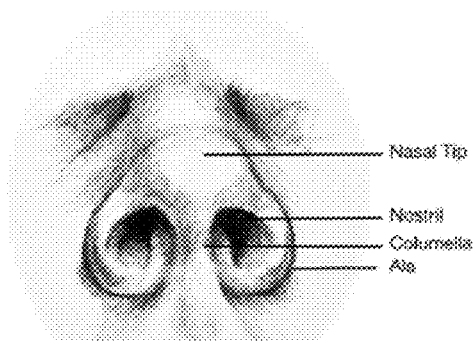
FIG. 32

Ears
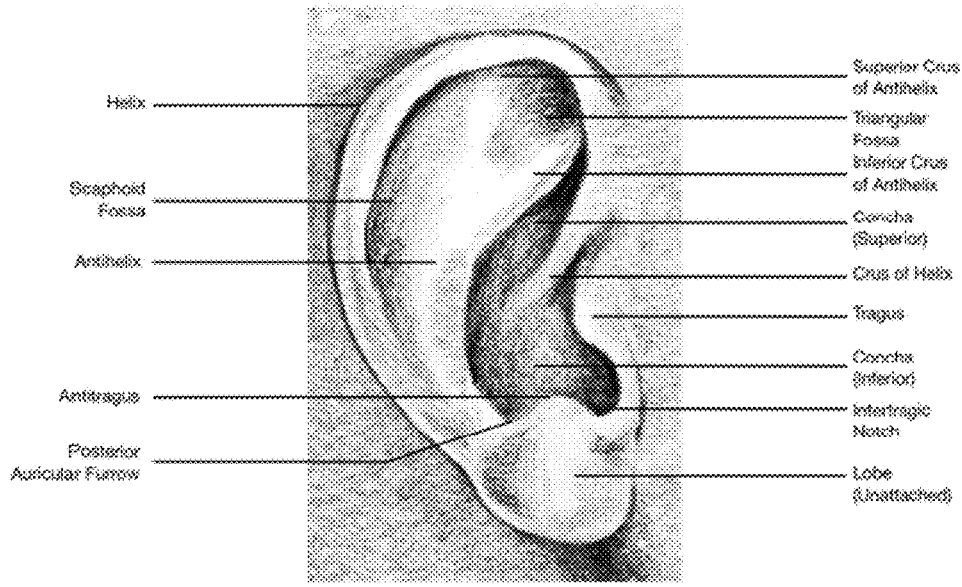
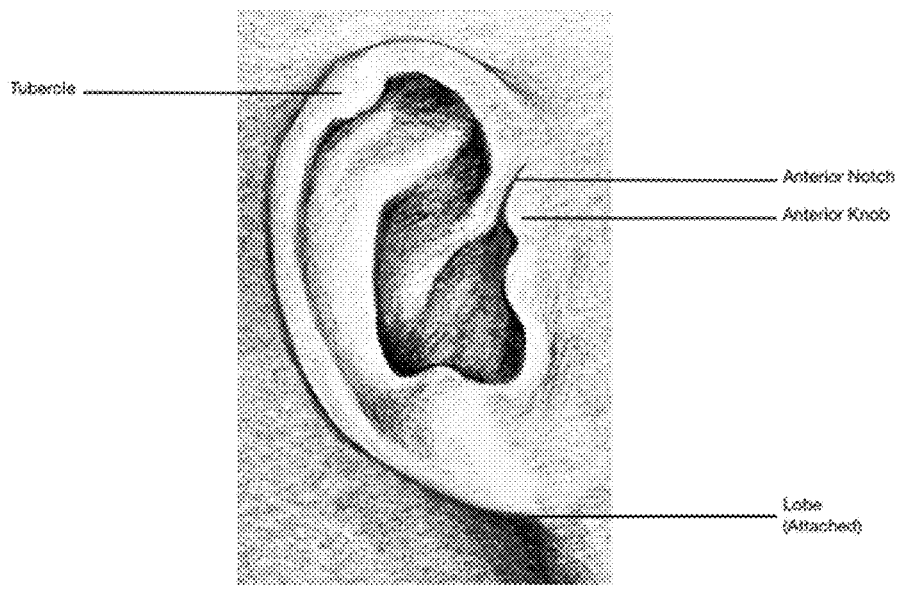
FIG. 34

Chin/Jawline
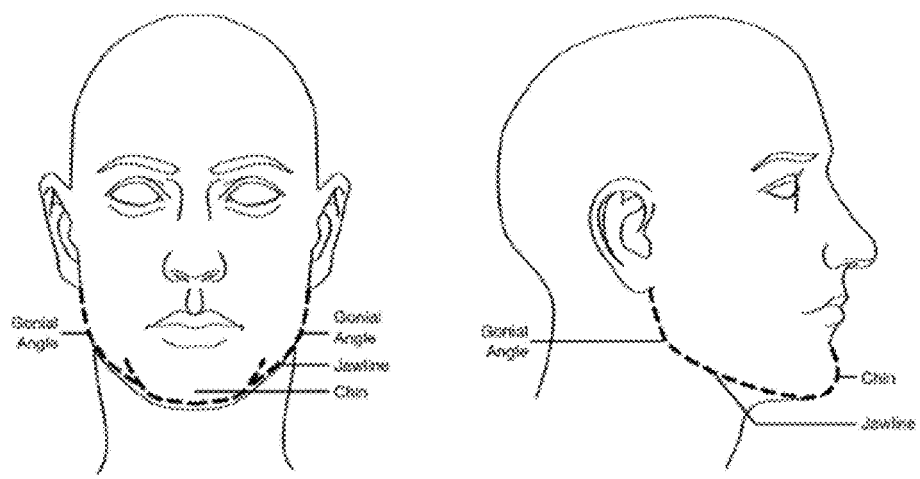
Neck
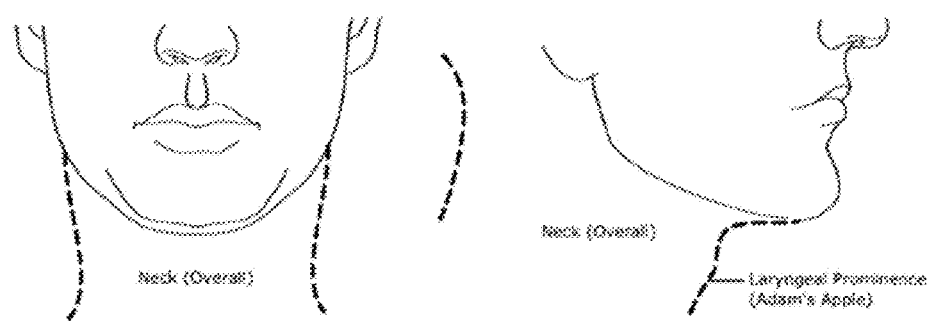
FIG. 36

FACIAL IDENTIFICATION TECHNIQUES

RELATED APPLICATION DATA

This application is a Continuation of U.S. patent application Ser. No. 15/092,328, filed Apr. 6, 2016, now U.S. Pat. No. 9,881,205, which claims the benefit of and priority under 35 U.S.C. § 119(e) to U.S. Patent Application No. 62/168,351, filed May 29, 2015, entitled "Facial Identification Techniques," each of which are incorporated herein by reference in their entirety.

BACKGROUND

While both finger and facial images exist as images for processing and comparison, there are key differences between the two:
- Fingerprint images are black and white while facial imagery can be color or black and white.
- Fingerprints are caused by touching a surface (which stabilizes the capture) while facial images are captured with little or no control over the subject.
- Finger details (ridge flows and minutia patterns) are a discrete type of image pattern whereas facial features vary widely across gender, race, age, hair, pose, lighting, facial obstructions, etc.
- There are many accepted courses and career tracks for the training of fingerprint examiners, whereas there are no current public courses for the training of facial examiners.

Human examiners can be presented with facial images for comparisons in two distinct ways:
- Computer based algorithms can be used to produce a list of candidates for review after searching a probe image. This is referred to as "Facial Recognition" or FR.
- Two images can be manually selected for review.

In both cases, it is up to the human facial examiner to analyze the two images and produce a final decision whether the person in both images is of the same person. This process has several commonly used definitions:
- Facial Examination (FE): A formal systematic examination of two facial images to determine if the same person is shown in both images. An example of this systematic examination technique, broadly accepted for use in fingerprint examinations, is called ACE-V (Analysis, Comparison, Evaluation, and Verification).
- Facial Identification (FI): The human-based examination of the similarities and differences between two facial images with the goal of determining if the same person is shown in both.

In any current operational environment using facial biometrics, the act of the FI is where a human facial examiner (or a group of examiners working together) is responsible for making a decision as to whether the same person is shown in two distinct images being compared.

BRIEF DESCRIPTION OF THE DRAWINGS

The exemplary embodiments of the technology will be described in detail, with reference to the following figures wherein:

FIGS. 28-37 show examples of accepted anatomical definitions of facial components.

DETAILED DESCRIPTION

Embodiments of systems and methods described herein can operationally ensure that a facial examiner follows specific predefined guidelines or best practices during a facial identification process. While accredited and accepted training for facial examiners evolve, an operational owner can integrate the appropriate guidelines or best practices directly into the actual facial identification processes used in real operational environments or training courses. Such guidelines or best practices can include a list of specific facial components that should be reviewed for every instance of a human facial examiner performing FI.

In one exemplary embodiment, the list of facial components includes, but is not limited to, one or more of skin, face/head outline, face/head composition, hairline or baldness pattern, forehead, eyebrows, eyes, cheeks, nose, ears, mouth, chin or jaw line, neck, facial hair, facial lines, scars, facial marks, and alterations. Other embodiments of the list can include a different set of fewer (or more) facial components. Such guidelines or best practices can also include instructions for each of these facial components to train, assist, or guide the facial examiner when performing the FI for that facial component.

Embodiments of systems and methods described herein directly integrate the list of predefined facial components into the FI process:
1. Providing a direct on-screen reference to the list of facial components and their associated anatomical terminology during the facial review.
2. Displaying the areas on the facial components on the face as defined by the guidelines or best practices.

3. Optionally ensuring the facial examiner looks at every facial component in the list.
4. Audit that every facial component in the list is reviewed by the facial examiner.

Figure 1:
FIG. 1 shows an exemplary setting of probe image eye locations.
Figure 2:
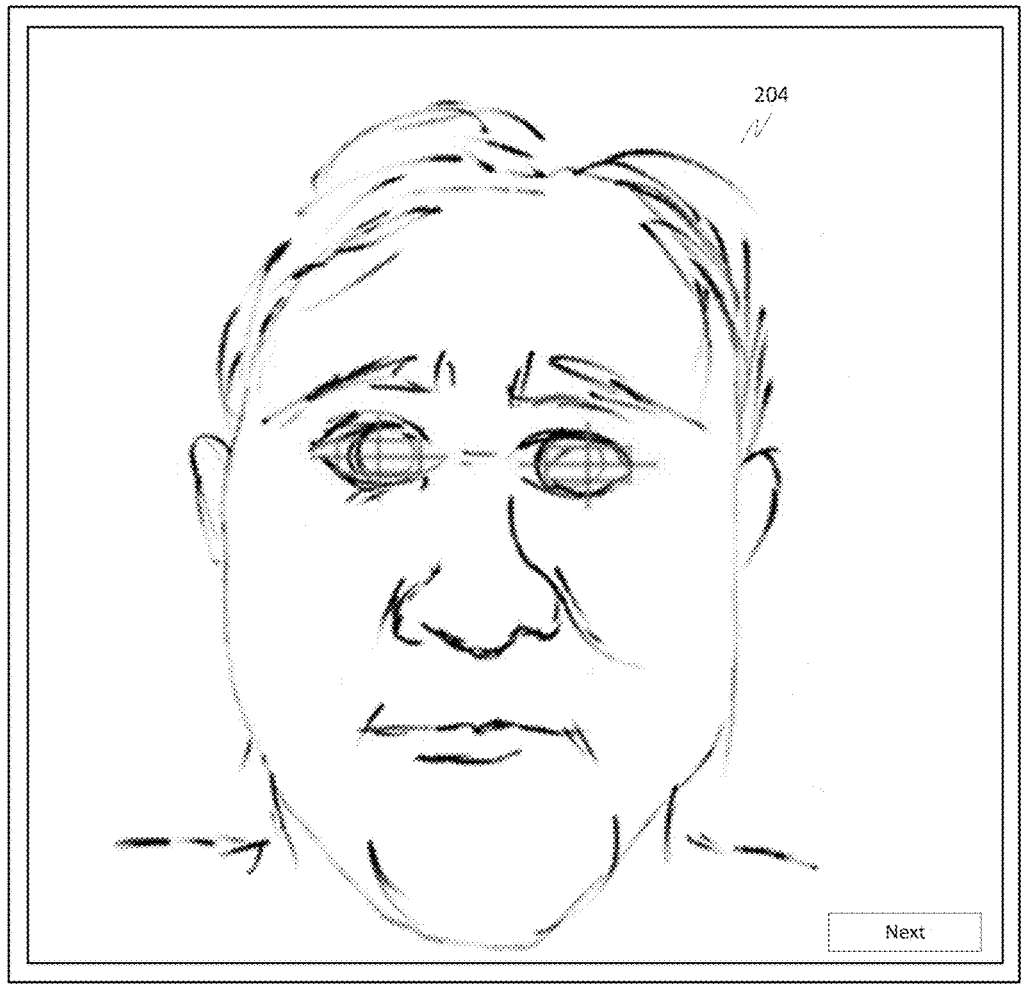
FIG. 2 shows setting candidate image eye locations.

Exemplary Steps:

Step 1:

The human facial examiner at a workstation sets the eye locations for both facial images (i.e., probe and candidate images). This operation can be done by manually reviewing and possibly (re)centering the eye locations over the left and right eye locations, as shown in FIG. 1 and FIG. 2 (Image 1 104 and Image 2 204). For example, one or more of the eye locations can be dragged-and-dropped to an updated center location using an input device such as a mouse. This setting of the eye locations is done to create landmarks so that all the facial components to be reviewed can be correlated to the eyes.

Figure 3:
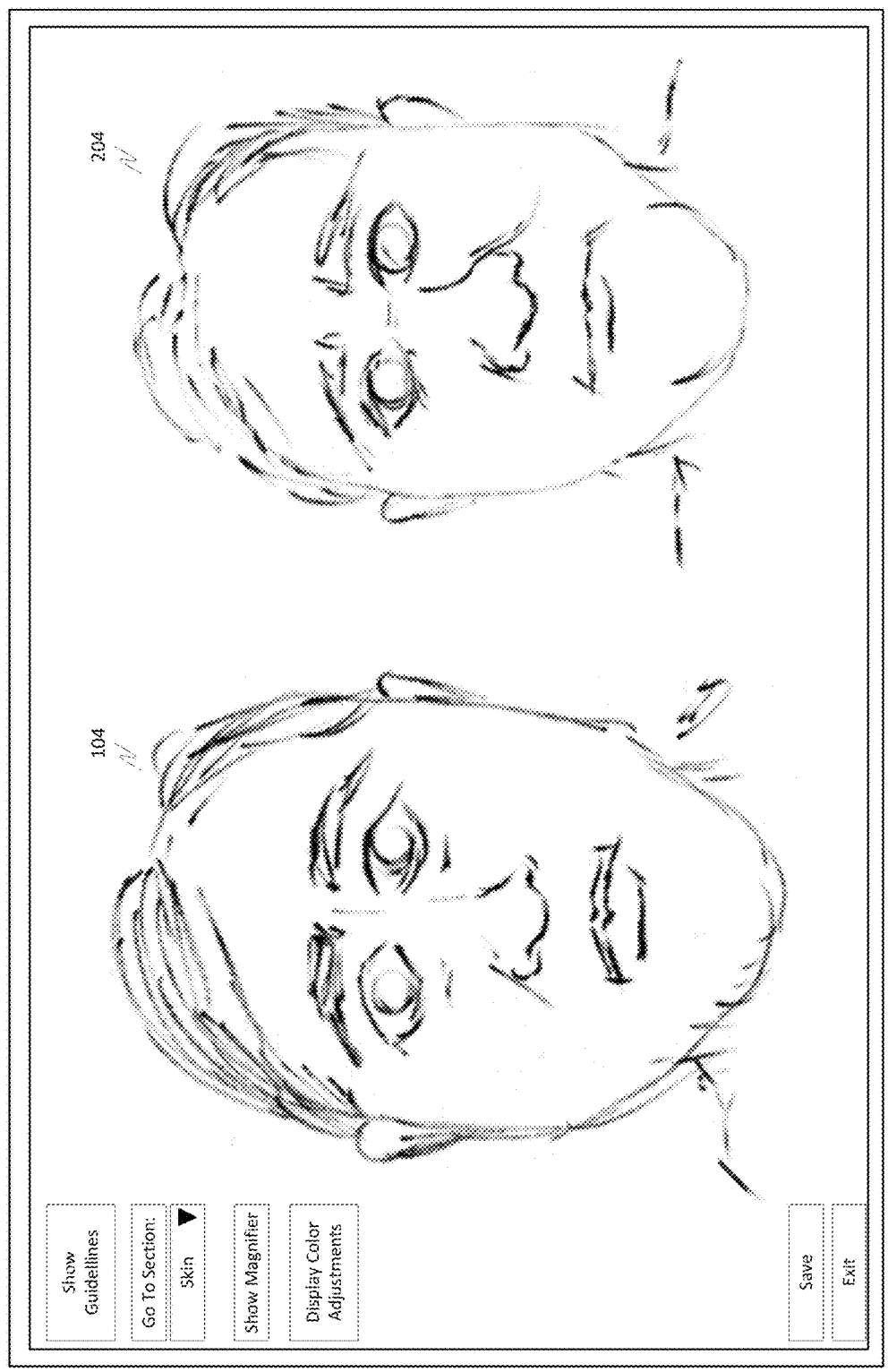
FIG. 3 shows an exemplary Side-by-Side probe and candidate images.

Step 2:

After the eye locations for both facial images are reviewed and accepted by the user at the workstation, both images 104 and 204 can be displayed side-by-side, as shown in the exemplary display in FIG. 3.

Figure 4:
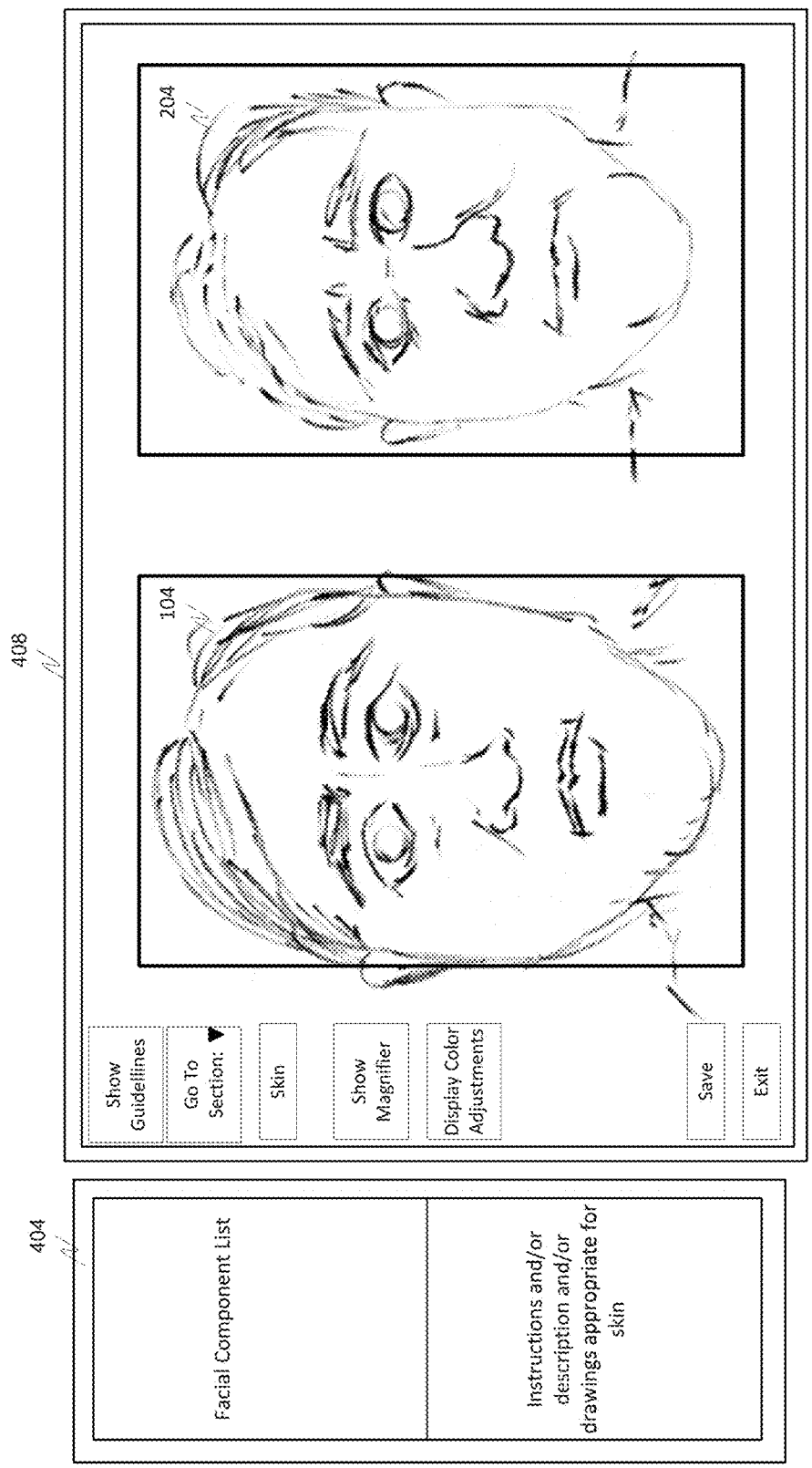
FIG. 4 shows an exemplary comparison of skin.

At this point, two windows 404 and 408 can appear as shown in FIG. 4 that are used during the enforced facial identification process.

1. In a first window 404 (which can optionally be a standalone window), any referenced document that the operational owner has decided to utilize in this facial identification process can be displayed to the user (i.e., facial examiner). The document can be placed in at any optimum location within the user's computer desktop environment.
2. The predefined list of the facial components mandated by the guidelines or best practice is displayed to the user in this window 404, which can also be placed in an optimum location within the user's computer desktop environment. In addition to displaying the list of facial components to be examined, other information, such as an identification information (ID), viewed status, and the results of the review can be associated with each facial component and optionally shown in one or more windows that can optionally be updated as the steps taken by the examiner are completed. Table 1 below provides an example of what may be presented to the user in this second standalone window.
   IDs may be associated with the facial components that must be reviewed; the IDs can enumerate and prioritize the facial components.
   The default state of Viewed Status can be NO.
   The default state of the Results (Similarity/Difference) can be NULL or empty.

TABLE 1

List of Facial Components

| ID | Facial Components | Viewed | Similarity (S)/ Difference (D) |
|---|---|---|---|
| A | Skin | Y/N | S/D/NA |
| B | Face/Head Outline | Y/N | S/D/NA |
| C | Face/Head Composition | Y/N | S/D/NA |
| D | Hairline/Baldness Pattern | Y/N | S/D/NA |
| E | Forehead | Y/N | S/D/NA |
| F | Eyebrows | Y/N | S/D/NA |
| G | Eyes | Y/N | S/D/NA |
| H | Cheeks | Y/N | S/D/NA |
| I | Nose | Y/N | S/D/NA |
| J | Ears | Y/N | S/D/NA |

TABLE 1-continued

List of Facial Components

| ID | Facial Components | Viewed | Similarity (S)/ Difference (D) |
|---|---|---|---|
| K | Mouth | Y/N | S/D/NA |
| L | Chin/Jaw line | Y/N | S/D/NA |
| M | Neck | Y/N | S/D/NA |
| N | Facial Hair | Y/N | S/D/NA |
| O | Facial Lines | Y/N | S/D/NA |
| P | Scars | Y/N | S/D/NA |
| Q | Facial Marks | Y/N | S/D/NA |
| R | Alterations | Y/N | S/D/NA |

Step 3:

At this point the user can sequence from facial component A through the last facial component to be examined during the FI process as shown in FIGS. 5-21. In one embodiment, the list of facial components identifies every facial component that must be examined for the FI process to be considered properly performed and in conformance with a particular standard, regulation and/or guideline. As the facial components are sequenced:

Visual boxes (or other highlighting technique(s)) can be shown to the user overlaid onto the facial images, which represent the specific facial component to be reviewed (See FIGS. 5-21);

The Viewed column is set from "No" to "Yes", as the user examines the facial component—this can optionally be automatically performed as the user/examiner views each specific facial component and steps to review the next; and The Similarity/Difference column can be set by the user indicating whether the specific facial component:
shows similarity (S),
does not show a similarity (D), or
cannot be evaluated (N/A).

The referenced guideline or best practice document can optionally be automatically repositioned to show each specific facial component within the context of the document.

Figure 5:
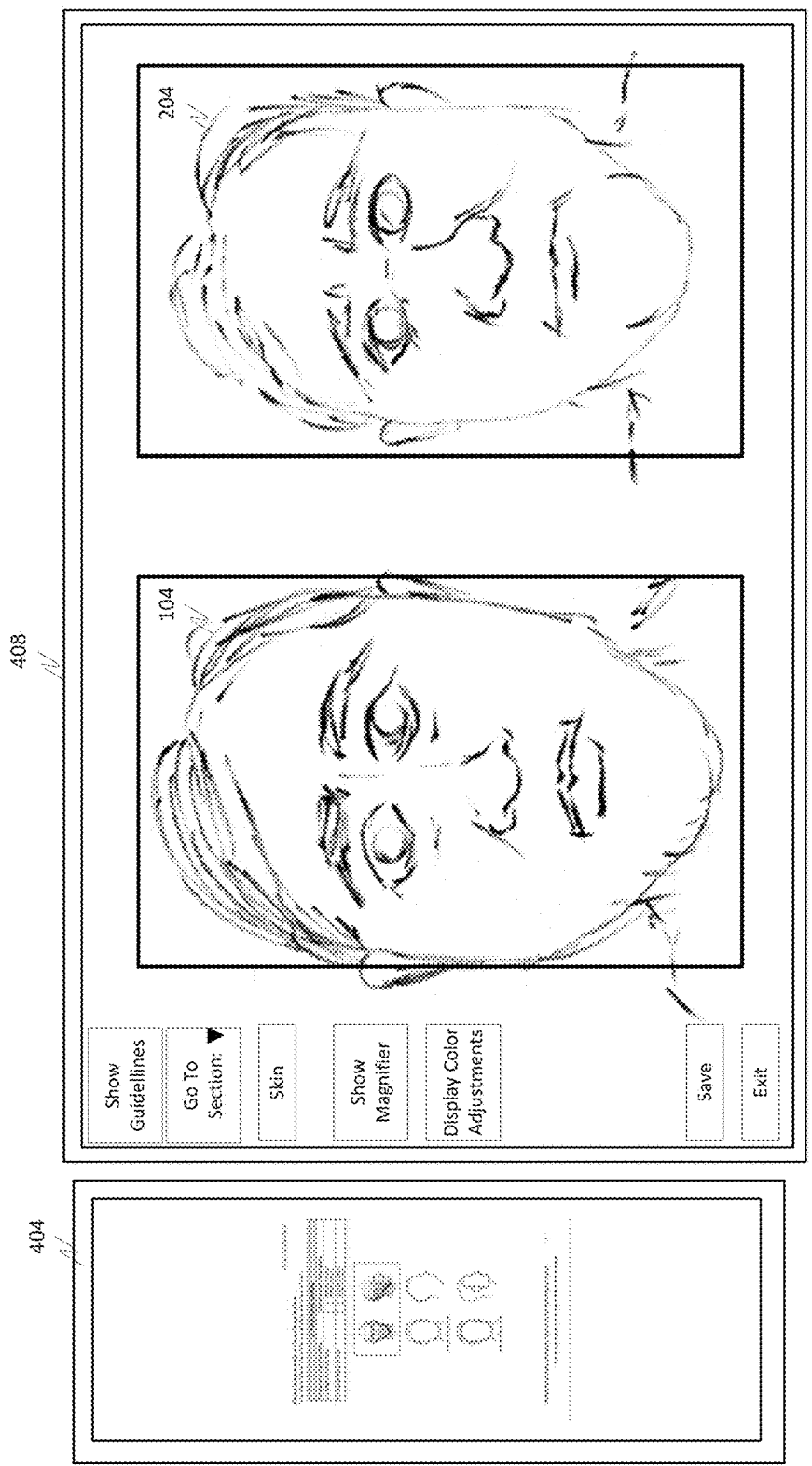
FIG. 5 shows an exemplary comparison of face/head outlines.
Figure 6:
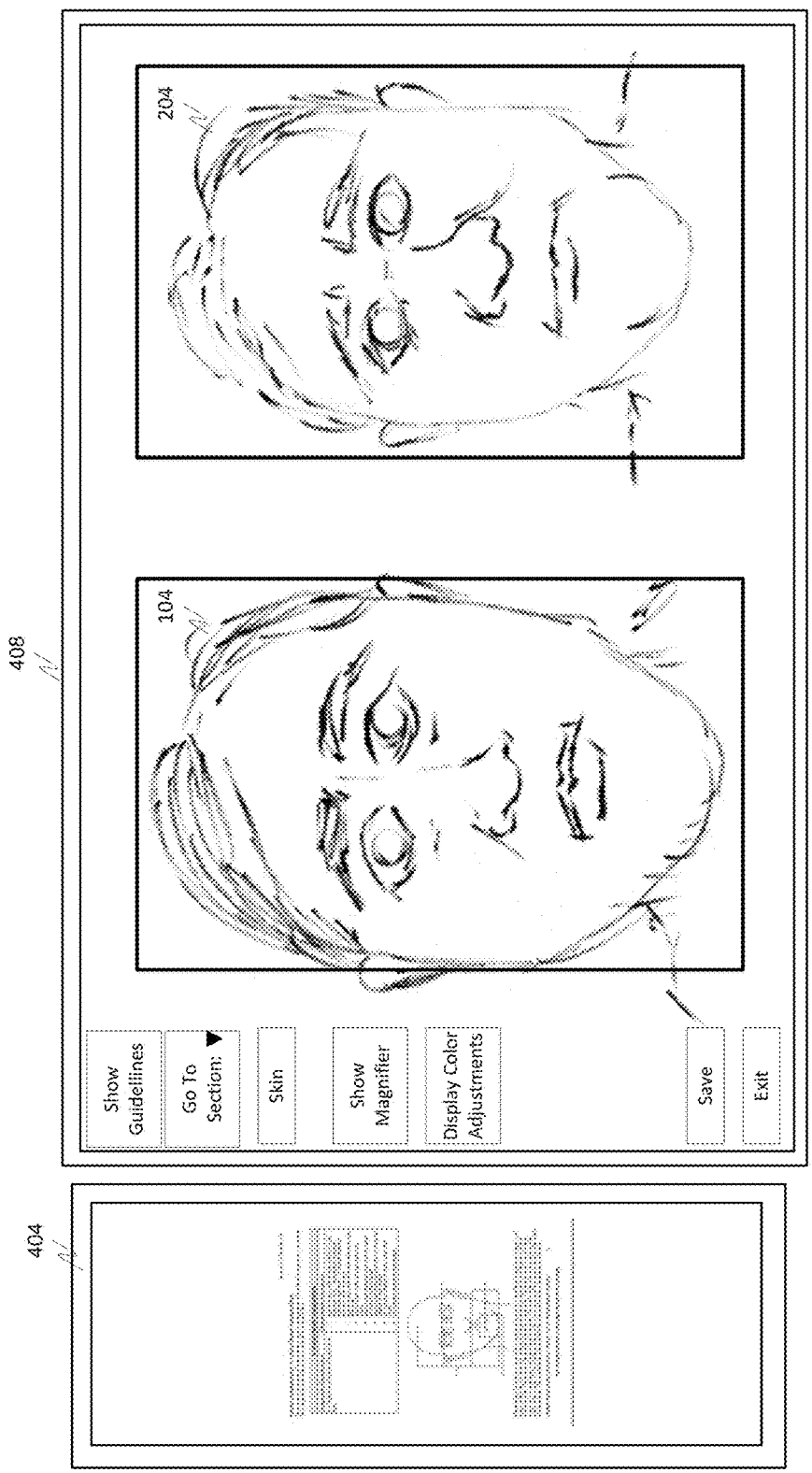
FIG. 6 shows an exemplary comparison of face/head composition.
Figure 7:
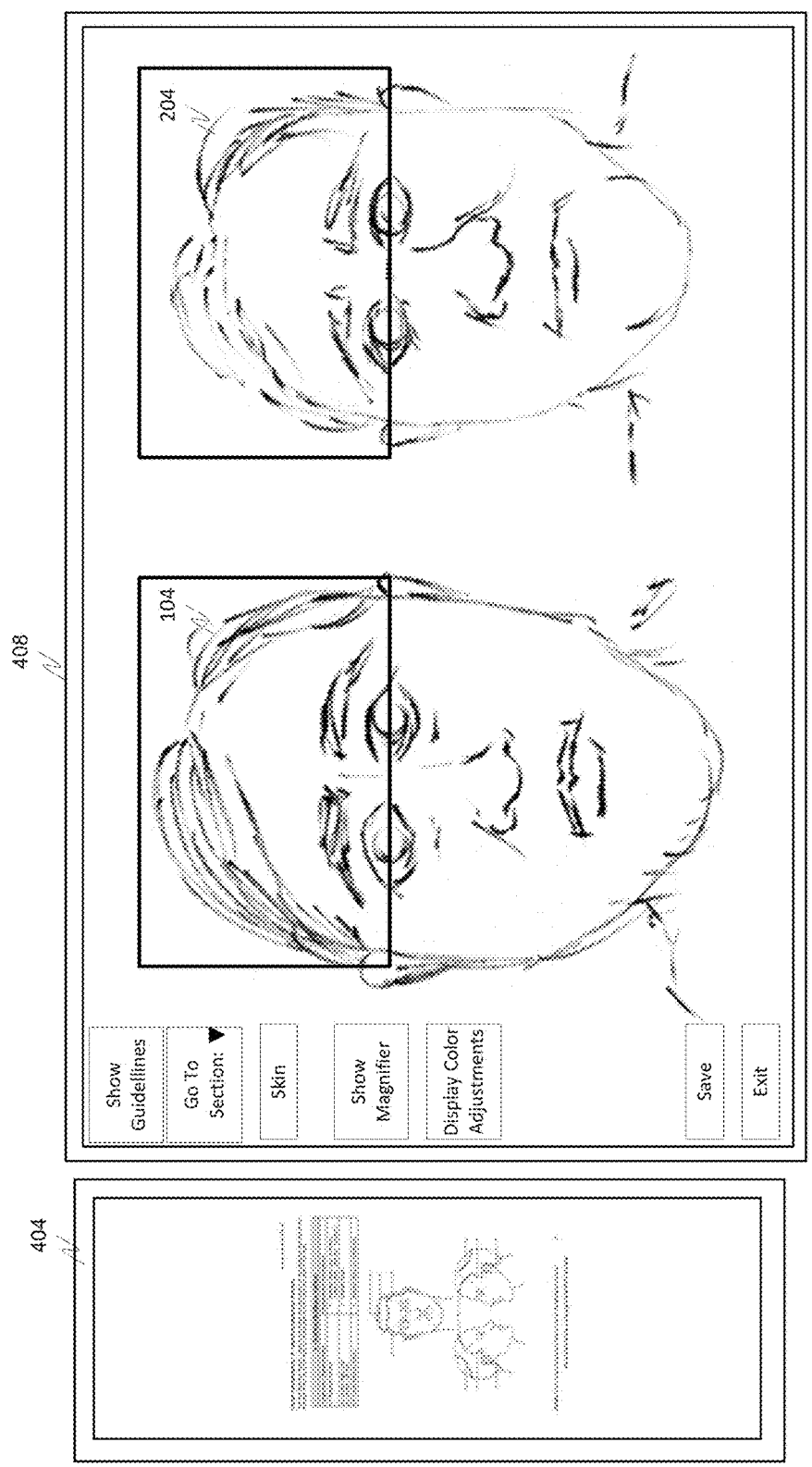
FIG. 7 shows an exemplary comparison of hair/baldness patterns.
Figure 8:
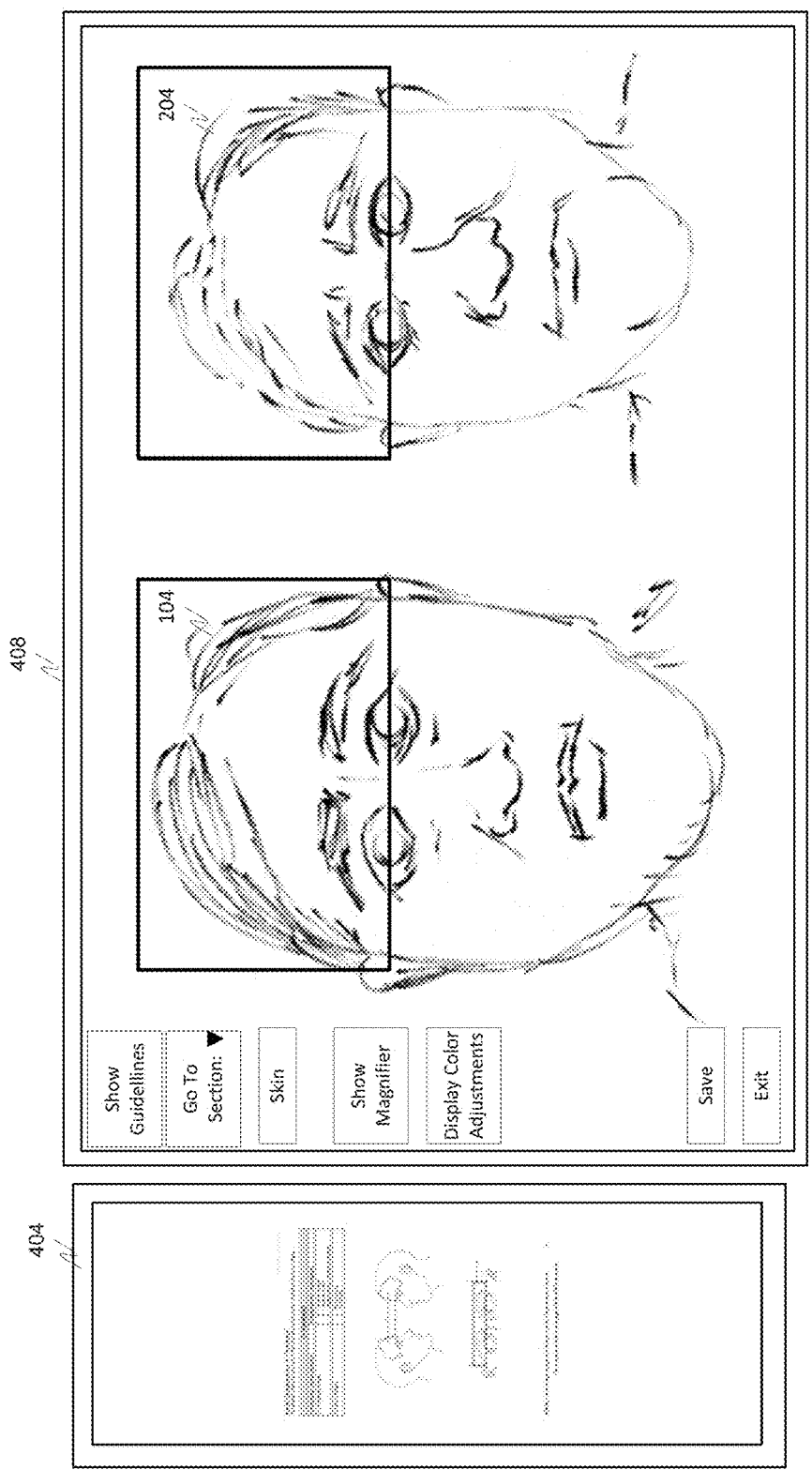
FIG. 8 shows an exemplary comparison of a forehead region.
Figure 9:
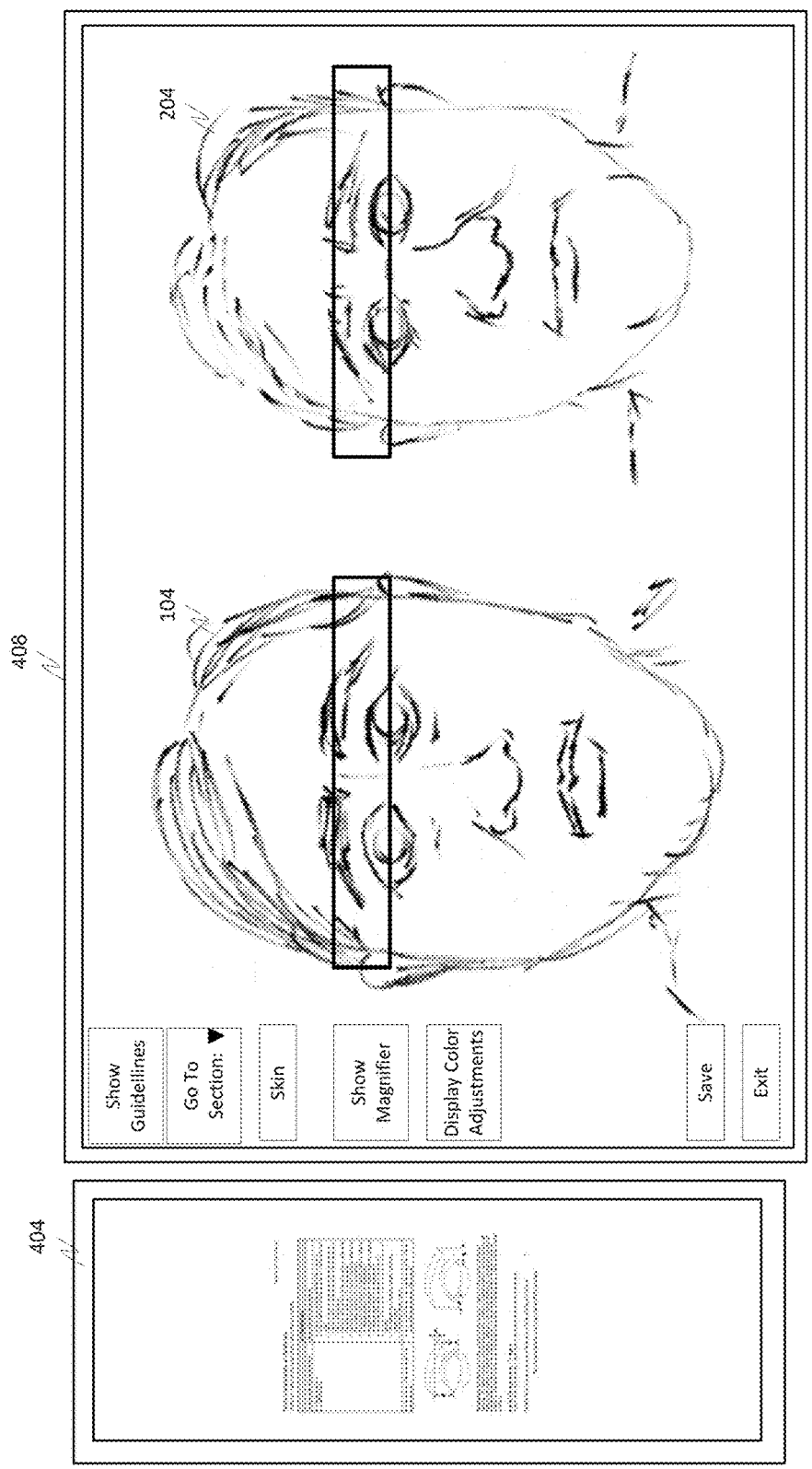
FIG. 9 shows an exemplary comparison of eyebrows.
Figure 10:
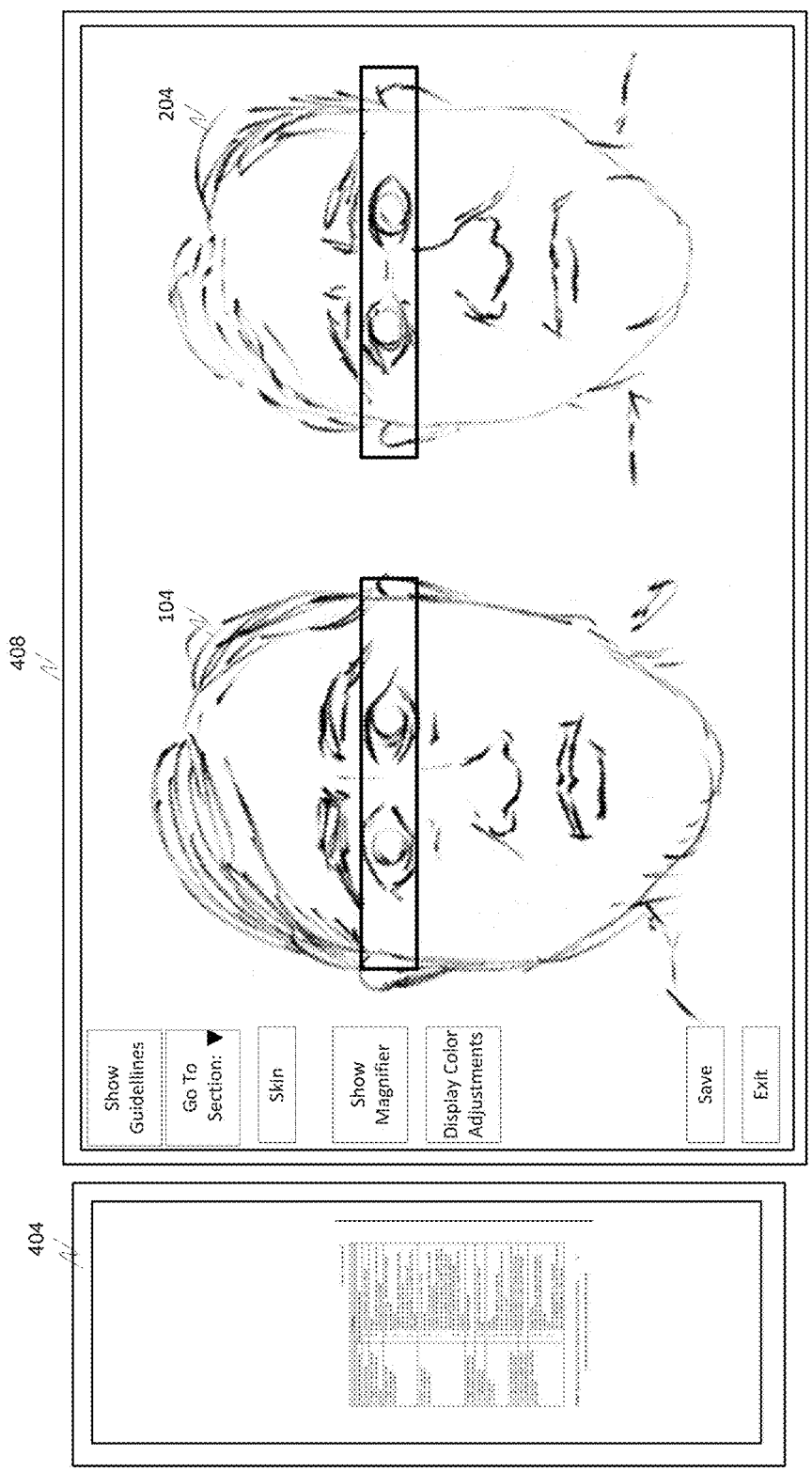
FIG. 10 shows an exemplary comparison of eyes.
Figure 11:
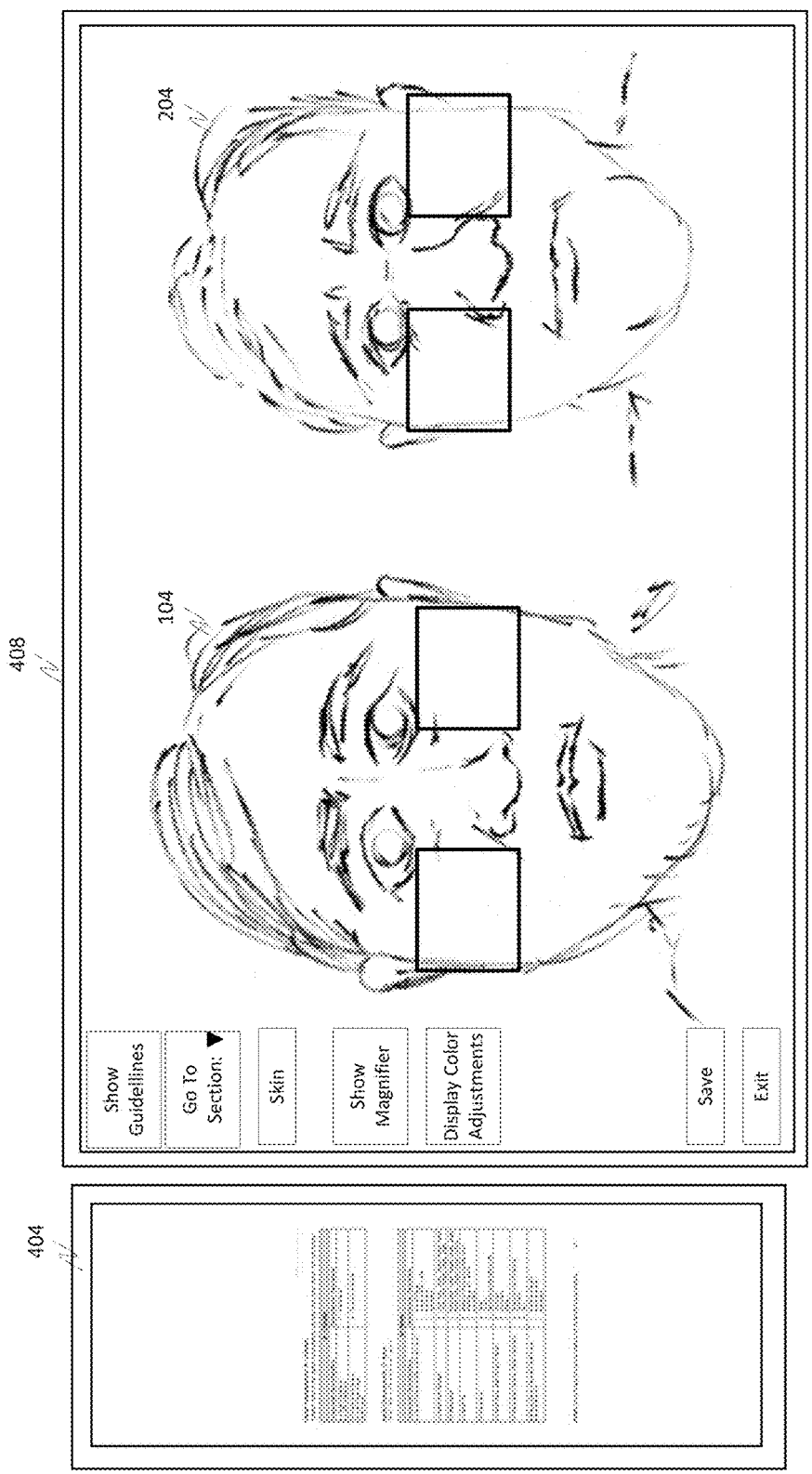
FIG. 11 shows an exemplary comparison of cheeks.
Figure 12:
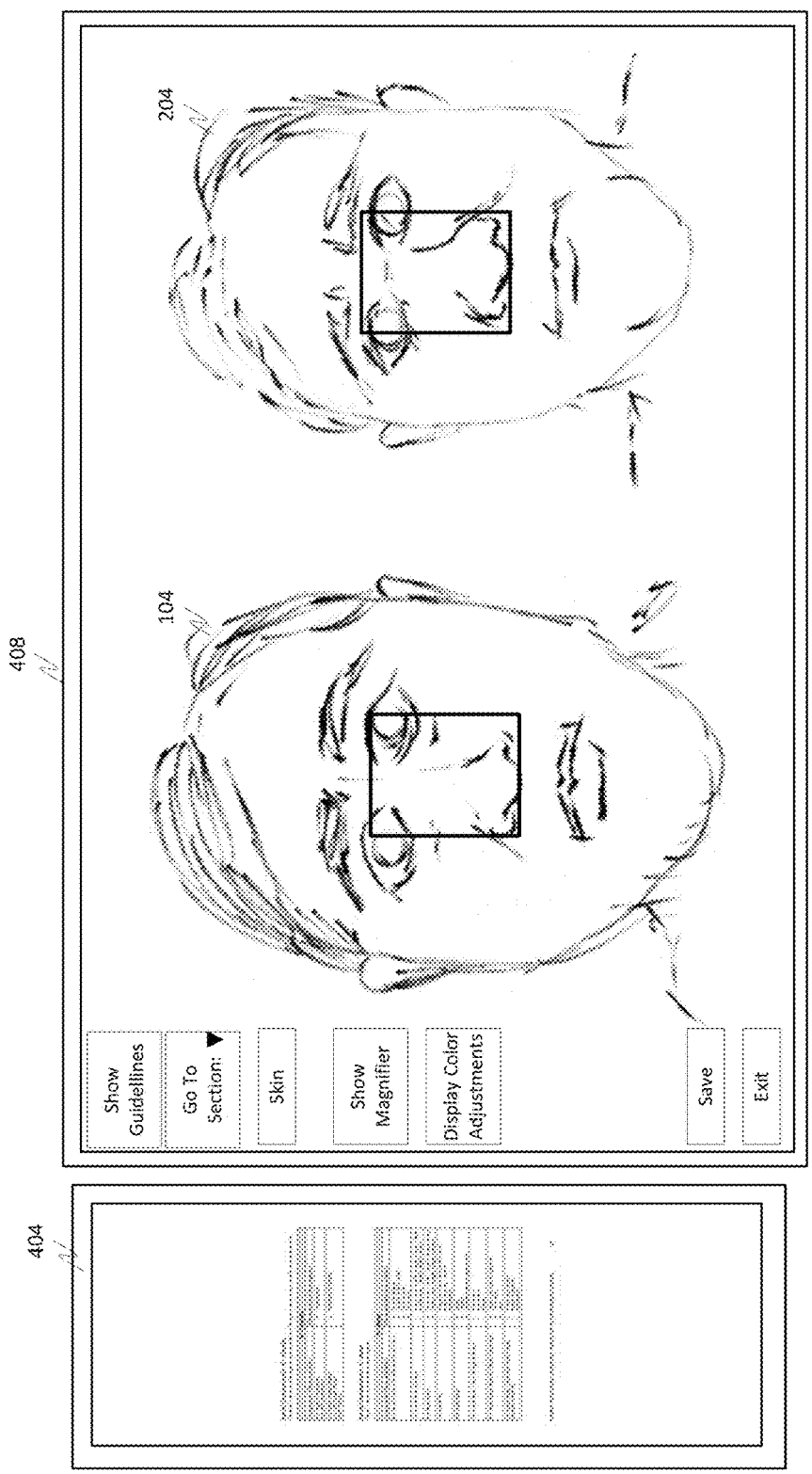
FIG. 12 shows an exemplary comparison of noses.
Figure 13:
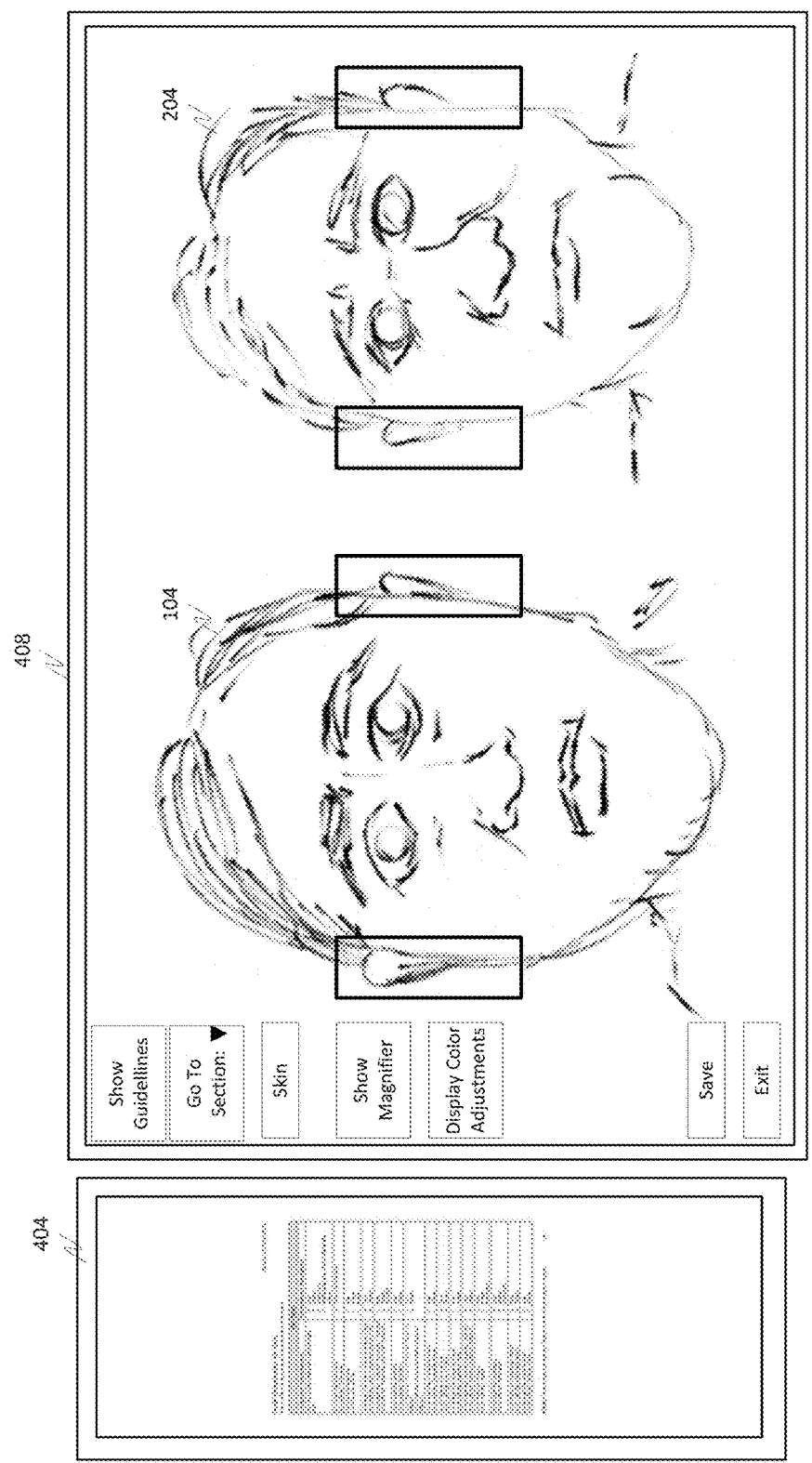
FIG. 13 shows an exemplary comparison of ears.
Figure 14:
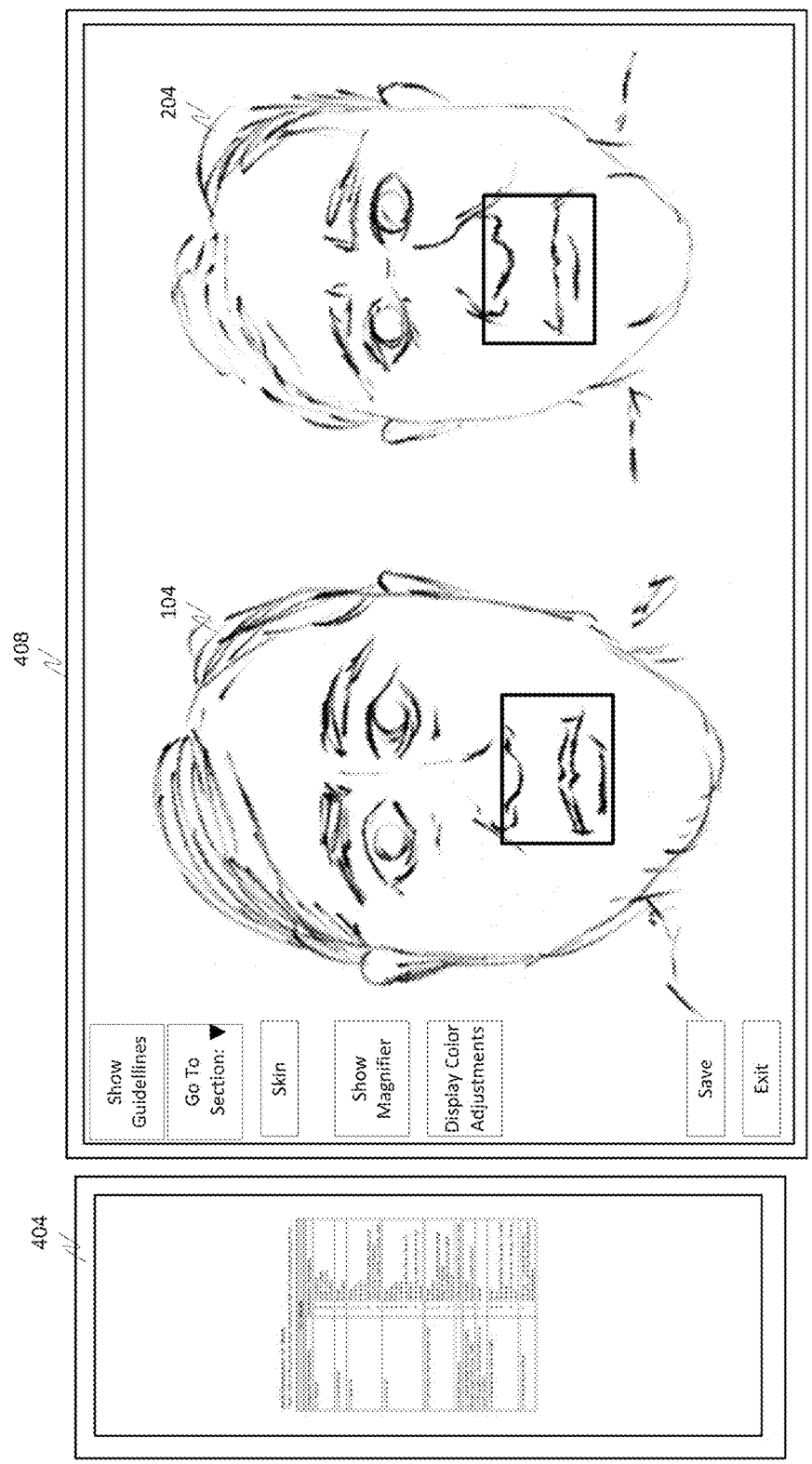
FIG. 14 shows an exemplary comparison of mouths.
Figure 15:
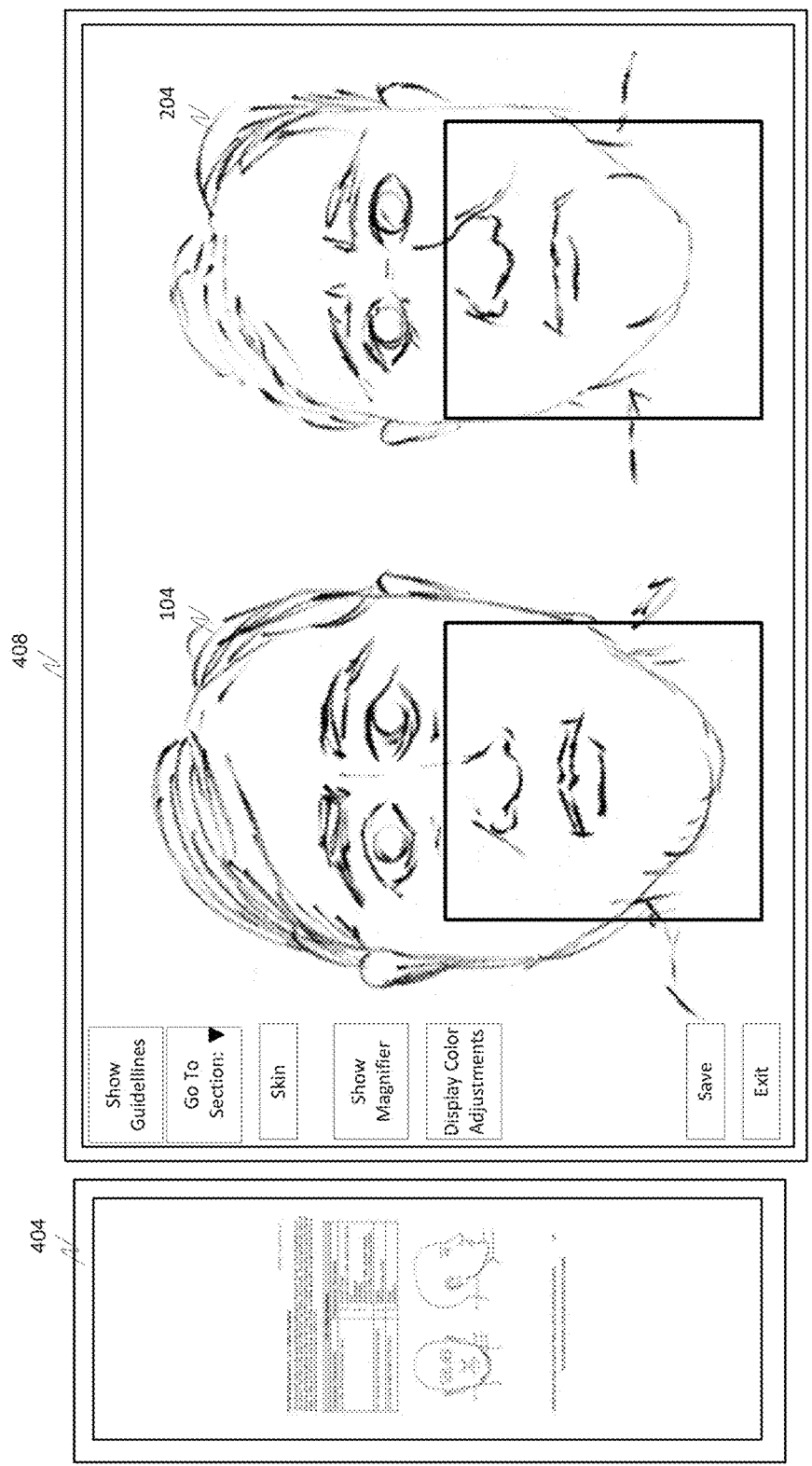
FIG. 15 shows an exemplary comparison of chin/jaw lines.
Figure 16:
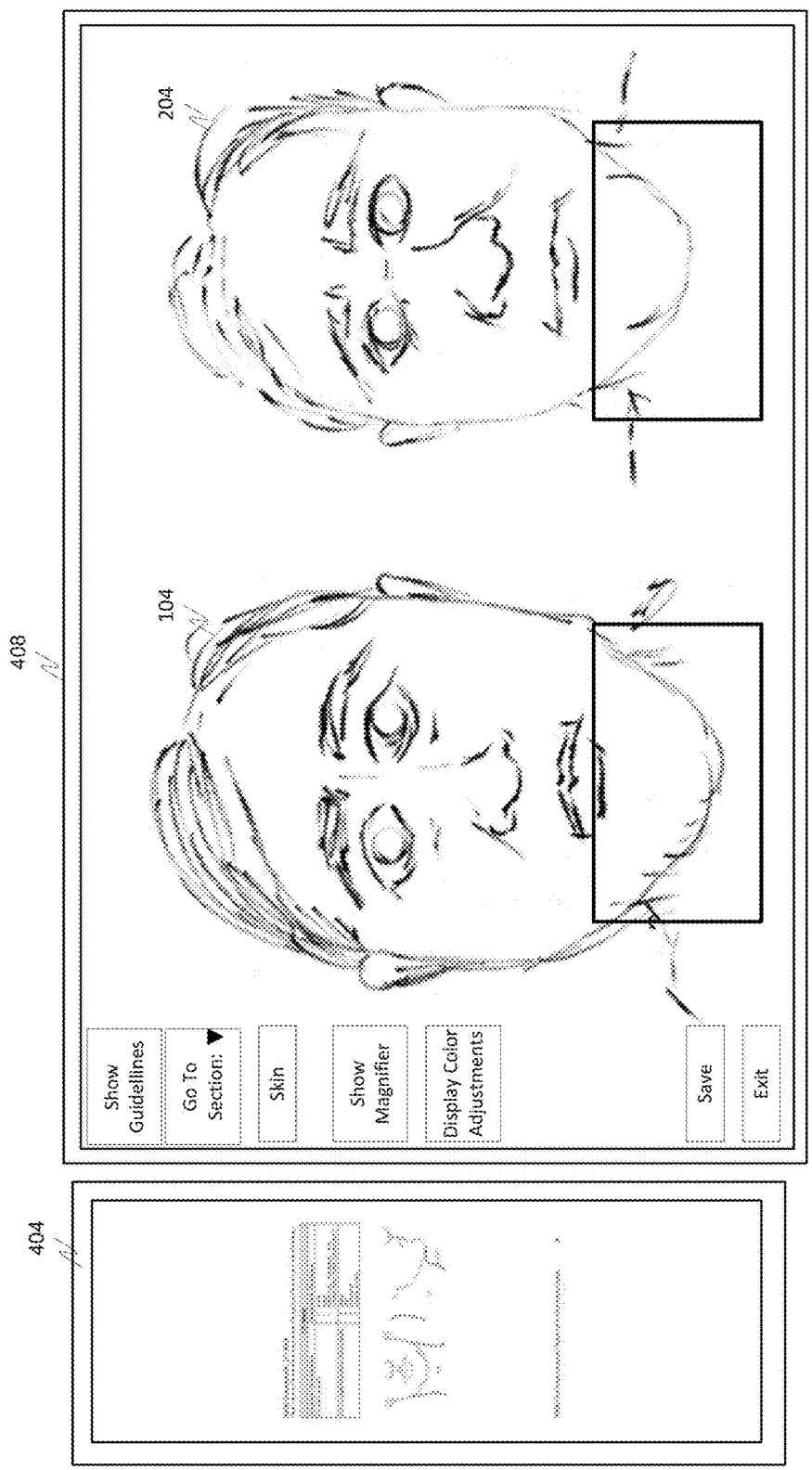
FIG. 16 shows an exemplary comparison of necks.
Figure 17:
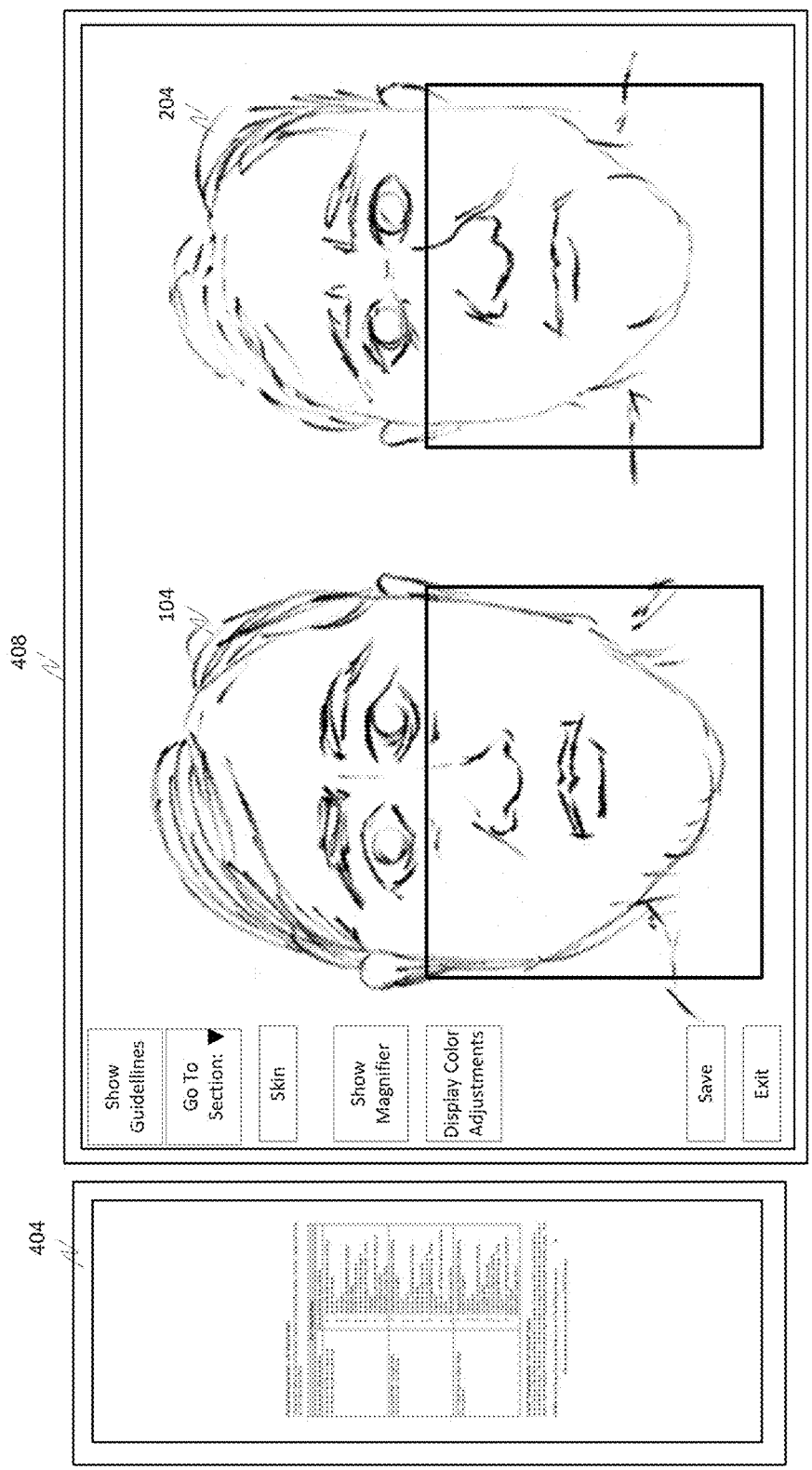
FIG. 17 shows an exemplary comparison of facial hair.
Figure 18:
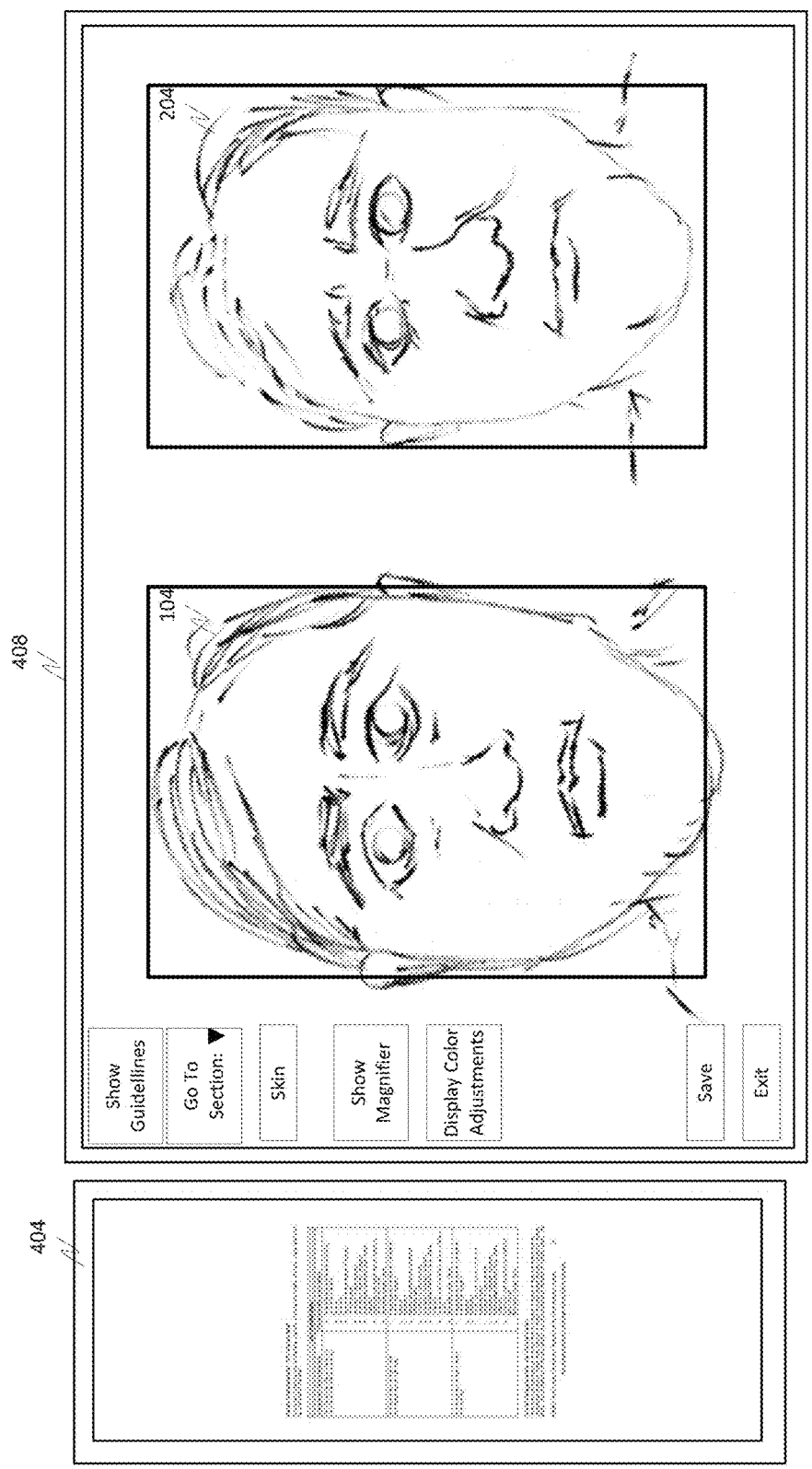
FIG. 18 shows an exemplary comparison of facial lines.
Figure 19:
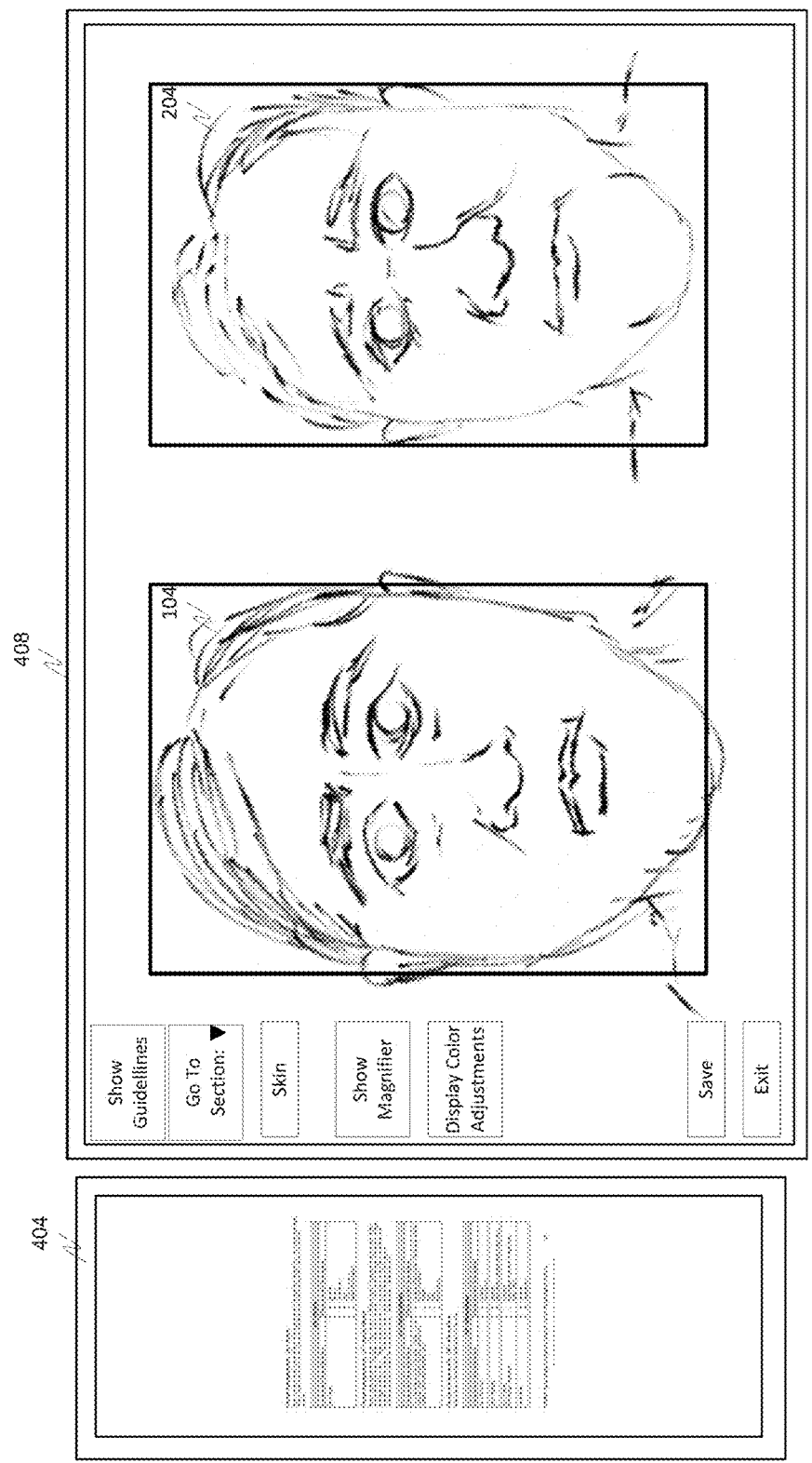
FIG. 19 shows an exemplary comparison of scars.
Figure 20:
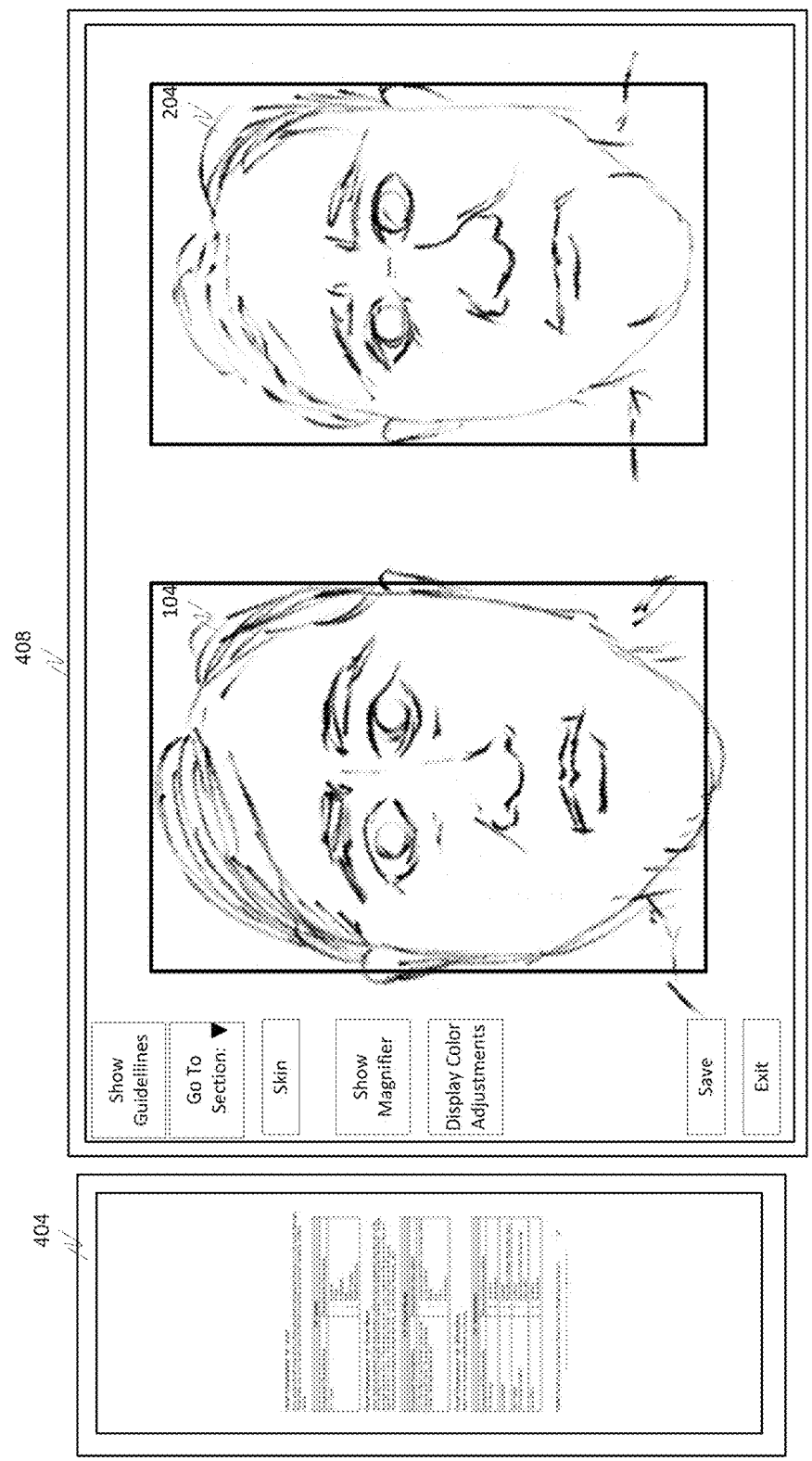
FIG. 20 shows an exemplary comparison of facial marks.
Figure 21:
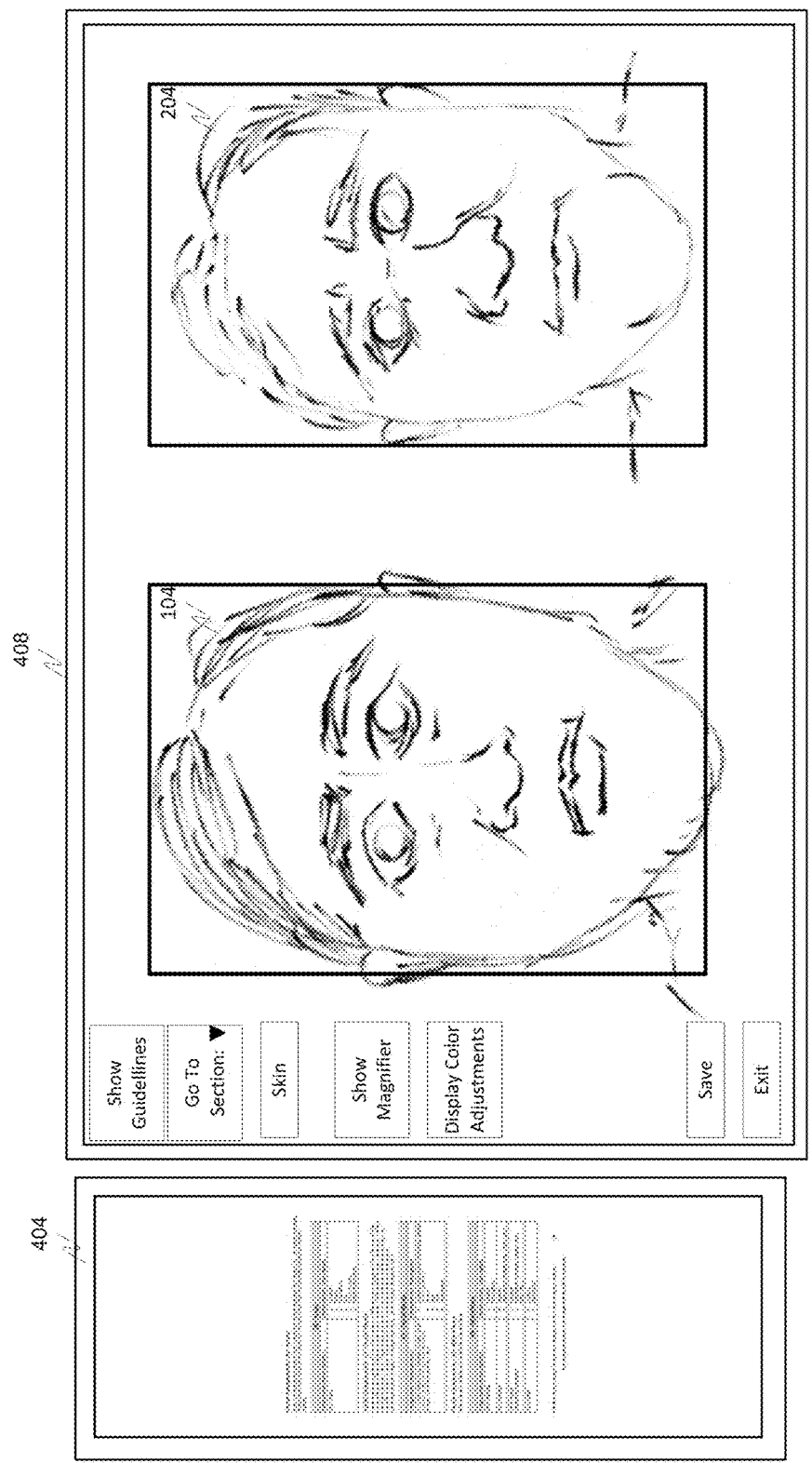
FIG. 21 shows an exemplary comparison of alterations.

It is to be understood that the order in which the facial components are examined may differ from that described below. As discussed, FIGS. 5-22 shown exemplary comparisons for various facial features. As illustrated in these exemplary Figures, a visual box(s) and/or highlight is placed around the feature(s) to be compared. Specifically, FIG. 5 shows an exemplary comparison of face/head outlines, with guidelines for the comparison shown in window 404. FIG. 6 shows an exemplary comparison of face/head composition, with guidelines for the comparison shown in window 404. FIG. 7 shows an exemplary comparison of hair/baldness patterns, with guidelines for the comparison shown in window 404. FIG. 8 shows an exemplary comparison of a forehead region, with guidelines for the comparison shown in window 404. FIG. 9 shows an exemplary comparison of eyebrows, with guidelines for the comparison shown in window 404. FIG. 10 shows an exemplary comparison of eyes, with guidelines for the comparison shown in window 404. FIG. 11 shows an exemplary comparison of cheeks, with guidelines for the comparison shown in window 404. FIG. 12 shows an exemplary comparison of noses, with guidelines for the comparison shown in window 404. FIG. 13 shows an exemplary comparison of ears, with guidelines for the comparison shown in window 404. FIG. 14 shows an exemplary comparison of mouths, with guidelines for the comparison shown in window 404. FIG. 15 shows an exemplary comparison of chin/jaw lines, with guidelines for the comparison shown in window 404. FIG. 16 shows an exemplary comparison of neck, with guidelines for the comparison shown in window 404. FIG. 17 shows an exemplary comparison of facial hair, with guidelines for the comparison shown in window 404. FIG. 18 shows an exemplary comparison of facial lines, with guidelines for the comparison shown in window 404. FIG. 19 shows an exemplary comparison of scars, with guidelines for the comparison shown in window 404. FIG. 20 shows an exemplary comparison of facial marks, with guidelines for the comparison shown in window 404. FIG. 21 shows an exemplary comparison of alterations, with guidelines for the comparison shown in window 404.

Figure 22:
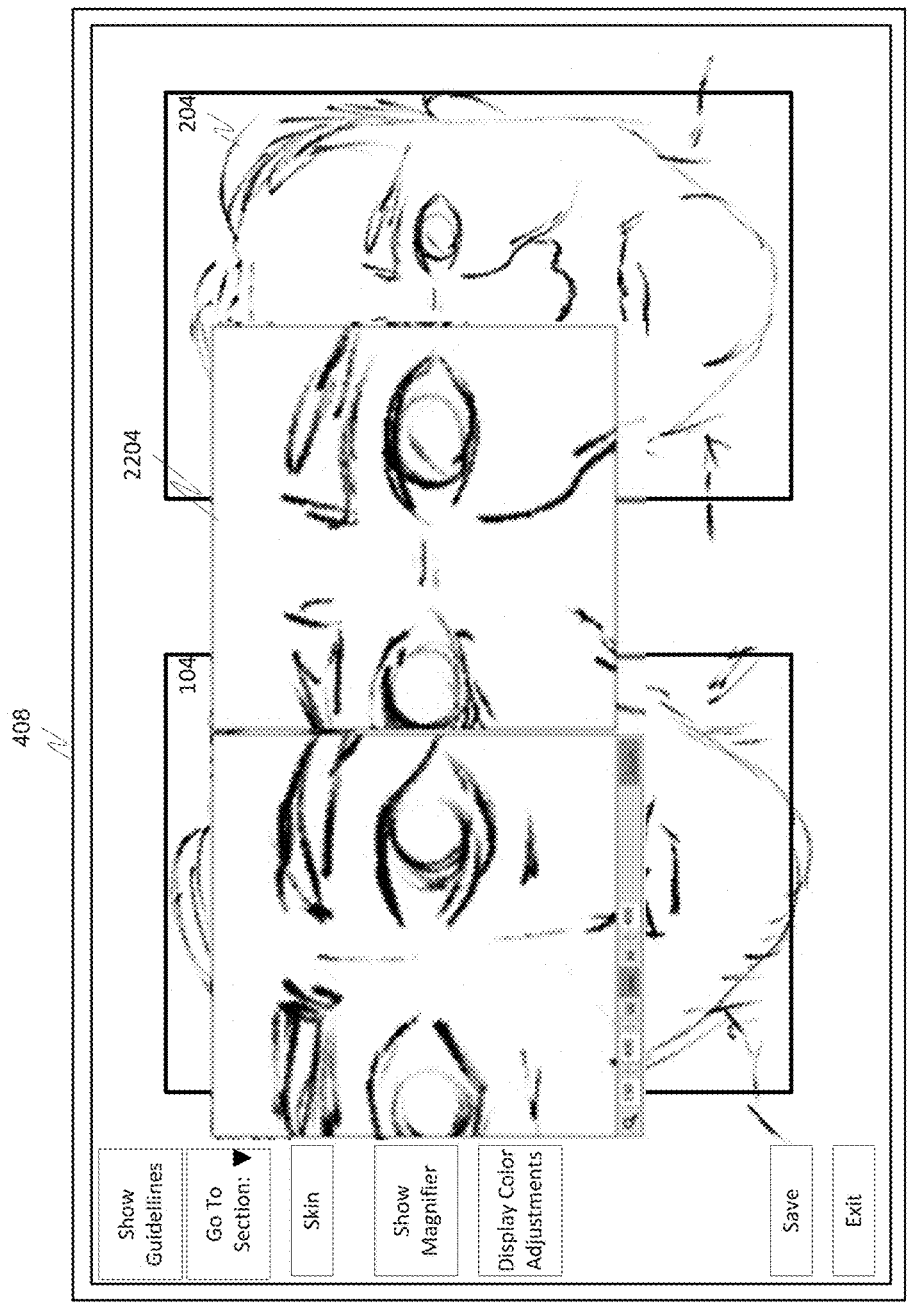
FIG. 22 shows an exemplary embodiment of embedded synchronized magnifiers.
Figure 23:
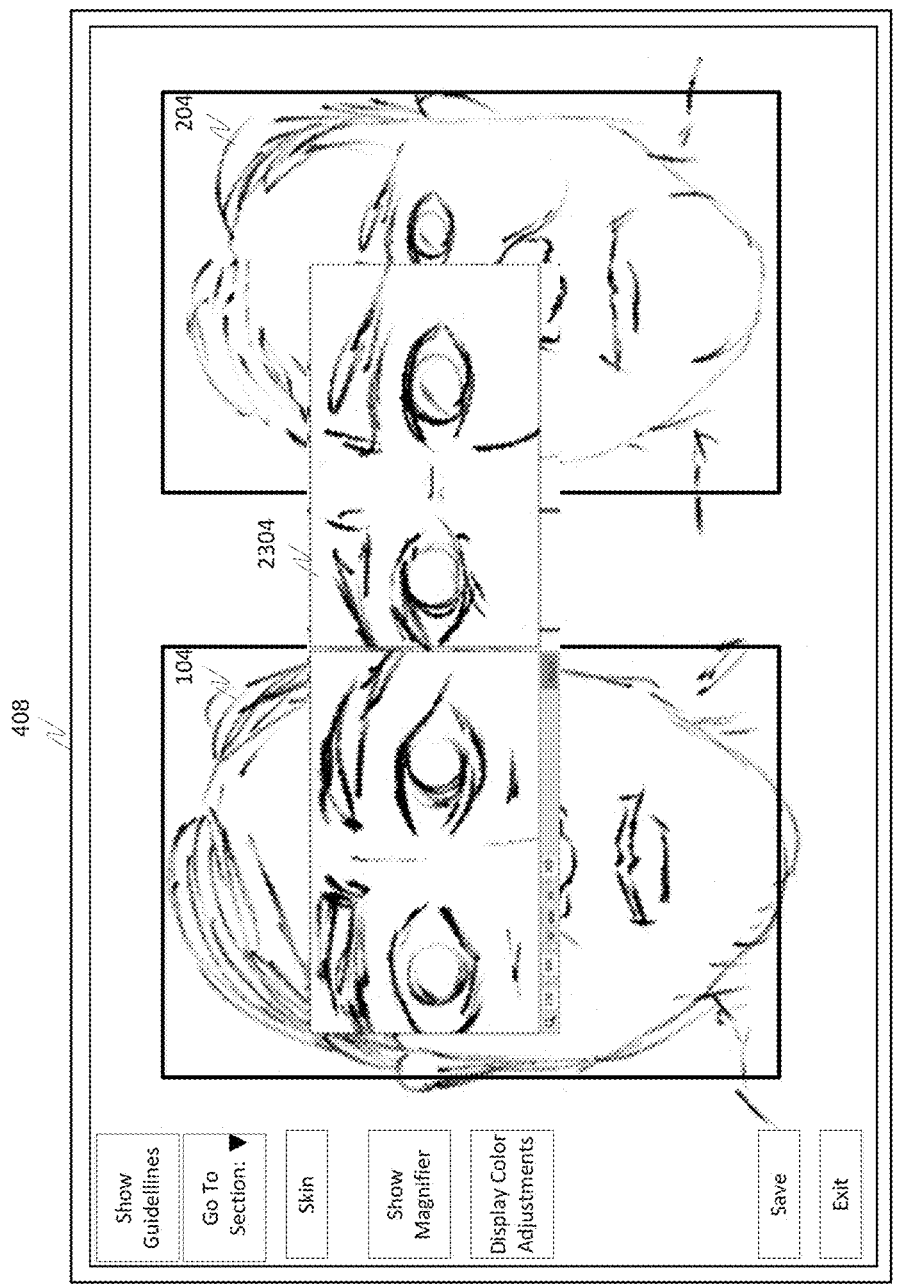
FIG. 23 shows an exemplary embodiment of a increased zoom feature of embedded synchronized magnifiers.
Figure 24:
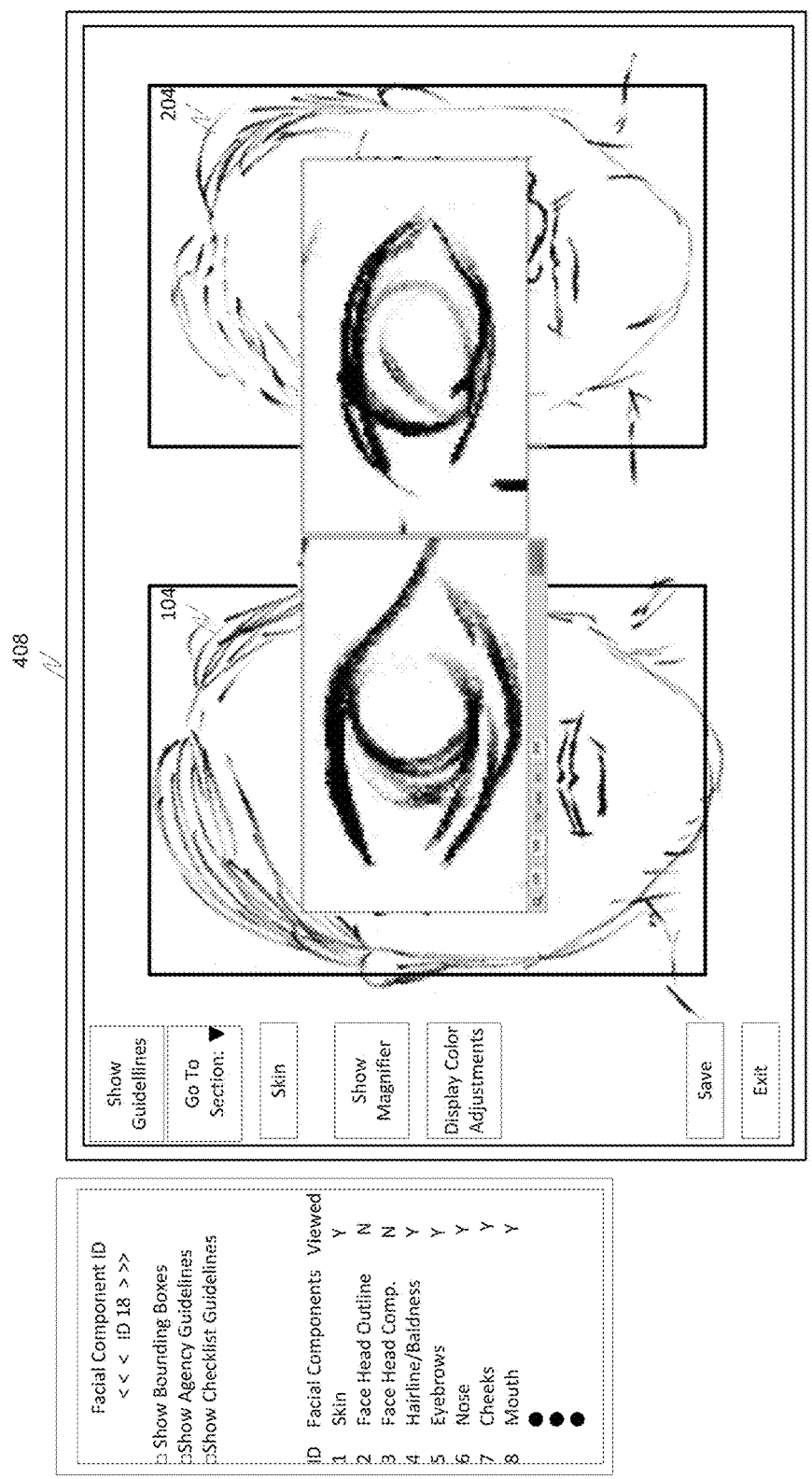
FIG. 24 shows an exemplary embodiment of an increased zoom of embedded synchronized magnifiers.

Step 4:

FIG. 22 shows an exemplary embodiment of embedded synchronized magnifiers 2204 where the eyes can be magnified to assist the user/examiner. These synchronized magnifiers can be moved to any part of the faces and are correlated to show the same portions of the faces 104 and 204 at the same time. FIG. 23 shows an exemplary embodiment of a first increased zoom feature 2304 of the embedded synchronized magnifiers and FIG. 24 shows a second exemplary embodiment of an increased zoom 2404 of embedded synchronized magnifiers. Here, the examiner has zoomed in significantly on one each in each of the probe and candidate images.

As each facial component is displayed to the user, a pair of synchronized magnification areas can optionally be displayed over the images allowing the user to zoom in on any discrete area, as shown, for example, in the above figures. At any time the size and zoom of the magnifiers can be controlled, updated or modified by the user.

Step 5:

In one embodiment, the user cannot complete the facial identification process unless:

All facial components in the list have been reviewed by the user; and

The user has specified whether for each facial component there is a similarity, a difference, or it cannot be evaluated.

The user can Exit the facial identification process at any stage in the process, but a decision as to whether the same person is in both images cannot be evaluated in such an event.

At the end of the entire facial identification process, a permanent auditing record may optionally be saved which confirms:

Two images were reviewed in accordance with a predefined process (e.g., guidelines or best practices);

On a specific date, a user on an operational workstation performed the facial identification controlled by the predefined process; and A final decision by the human examiner was arrived at.

Figure 25:
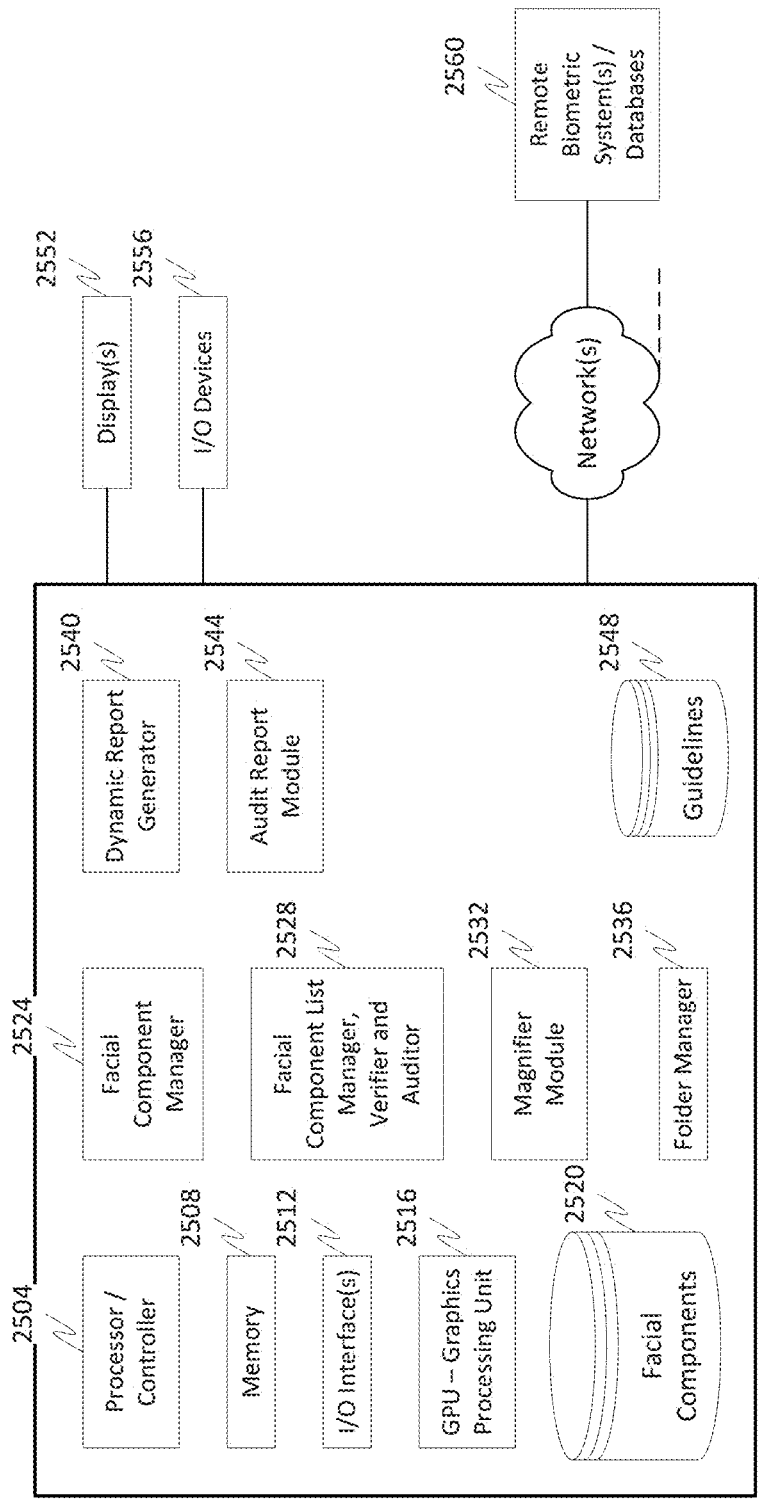
FIG. 25 shows an exemplary facial identification system.

FIG. 25 illustrates an exemplary system that can be used in conjunction with the above steps. The exemplary system includes a processor/controller 2504, memory 2508, I/O interface 2512, GPU 2516, facial components database 2520, facial component manager 2524, facial component list manager, verifier and auditor 2528, magnifier module 2532, folder manager 2536, dynamic report generator 2540, audit report module 2544, guidelines 2548, one or more displays 2552, one or more I/O devices 2556, and one or more remote biometric system(s)/databases/back-end systems 2560 (connected via the network(s)).

In operation, and in accordance with one exemplary embodiment, the system can be configured to resemble an email system. While other configurations are certainly possible, the emulation of an email system in terms of workflow at least assists with management and organization of the various images.

In accordance with one exemplary embodiment, the facial component manager 2524, in conjunction with the processor 2504, memory 2508, GPU 2516 and facial components database 2520 present a probe sample to the user at display 2552. This probe sample can be forwarded to a back-end system, such as remote biometric system 2560 to perform initial matching. Once sent, the folder manager 2536 can place the sent probe sample in a "sent folder"—the "sent folder" representing that the probe sample has been sent away for a search to be done by the back-end system 2560.

In conjunction with the search being sent out, a demographic filter and/or other filtering criteria can be sent with the image to help reduce the number of false positives received back from the back-end system.

On receipt of the results from the back-end system 2560, an indication can be placed in an "Inbox" by the folder manager 2536 alerting the user/examiner that there are probe and candidate samples ready to review (these results can be stored in the facial components database 2520). The GPU 2516 can provide to the user/examiner, on displays 2552, a candidate screen that shows all candidates returned by the back-end system 2560. This candidate screen, in conjunction with the facial components database 2520 and facial component manager 2524, can be filtered to reduce the number of candidates. For example, a user/examiner can select Yes, No or Maybe, to reduce the number of candidates to a more manageable number with the No candidates optionally being removed from the display.

Next, the user/examiner can perform a detailed review of the probe sample to one or more of the candidates as shown in FIGS. 3-25. During the comparison, the user/examiner can one or more of calibrate the faces, perform a visual alignment of the faces, adjust scaling, adjust colors, and in general adjust any one or more of the characteristics of the probe and candidate sample either in unison or separately. In general any type of image adjustment can be performed including one or more of invert, color channel adjustment, greyscale adjustment, CYMK adjustment, or the like.

As the user/examiner reviews each of the facial characteristics, the facial component list manager, verifier and auditor 2528, in conjunction with the processor 2504, facial component manager 2524 and facial component database 2520, tracks the actions and records the results of the comparisons. The user/examiner during this process can take snapshots of particular features of interest with these snapshots being captured and added into a report which is being dynamically generated by the dynamic report generator 2540. These snapshots can then optionally be supplemented with one or more comments from the user/examiner.

Also, at any time, the guidelines 2548 can be retrieved and displayed to the user/examiner. These guidelines can be dynamically liked to facial features such that if the user/examiner clicks on a particular feature (such as the eyes) the corresponding guidelines (such as in a PDF, text or other document format) for eye comparison can be displayed—such as the guideline shown in FIGS. 10-21 in windows 404.

Optionally, the audit report module 2544 can keep track and store one or more actions taken by the user/examiner, with the stored information usable for one or more of training, to confirm lack of biases, to identify errors and/or to ensure any applicable guidelines have been complied with. This audit trail can then be stored in the facial components database 2520 (or in general at any location and/or printed or sent to a destination such as via email) along with any information about the probe and/or candidate.

Figure 26:
FIG. 26 is a flowchart showing an exemplary method of performing facial recognition.

Optionally, the dynamic report generator 2540 can generate one or more reports. These reports can be compiled at the end of the review process (e.g., a finalization report) and/or dynamically created as the comparisons are made. As one example shows in FIG. 26, the report 2604 includes one or more sections populated with information regarding comparison decisions that were made. The exemplary sections include: "Snapshot", "Feature", "Same/Different", "Snapshot Images", "Comments", and "Data Path.". Snapshot can indicate a sequence number for the snapshot. Feature can indicate which feature the snapshot is for. Same/Different can represent whether the examiner believes the feature is the same or different. Snapshot images can include images of the comparison. Comments can include any examiner comments and data path can include information regarding the source file for the captured images.

As discussed above, the system can optionally be configured in an email-like manner. Thus, the system can have, for example, a reviewed folder, indicating that the examiner has reviewed and/or completed the comparison. The system can also optionally include a "needs attention" folder for situations where there has been an anomalous error.

For all of the various information, captures, reports etc. described herein, metadata can be associated with that information and can optionally be used for sorting (name, date, ID, etc.) or the like.

Figure 27:
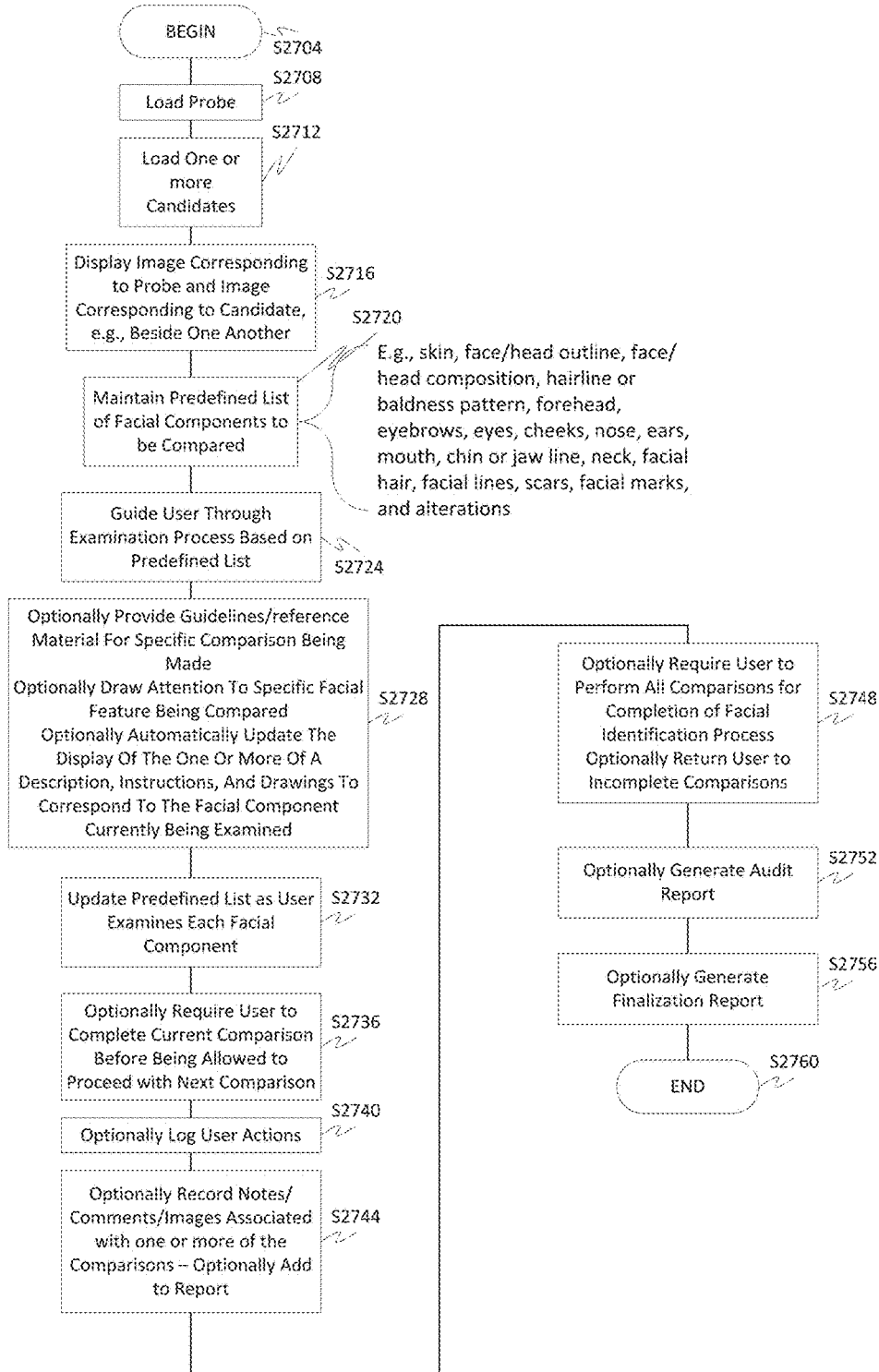
FIG. 27 shows an exemplary report.
Figure 30:
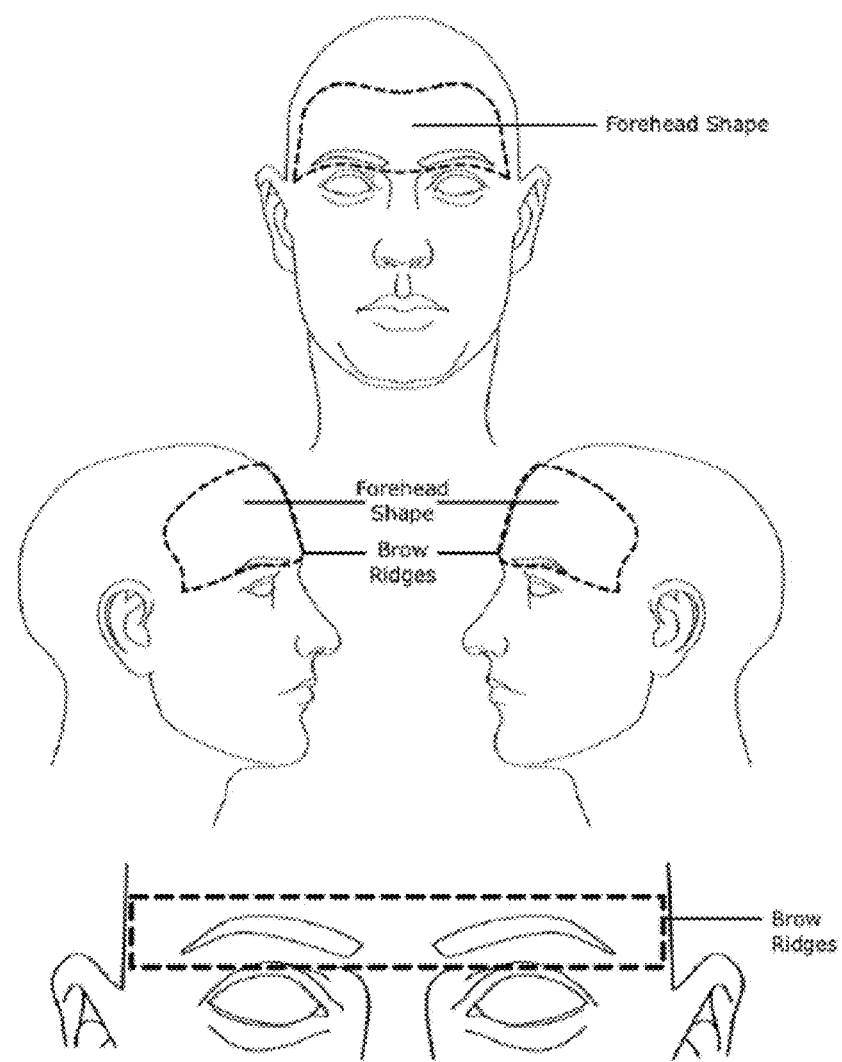
Figure 31:
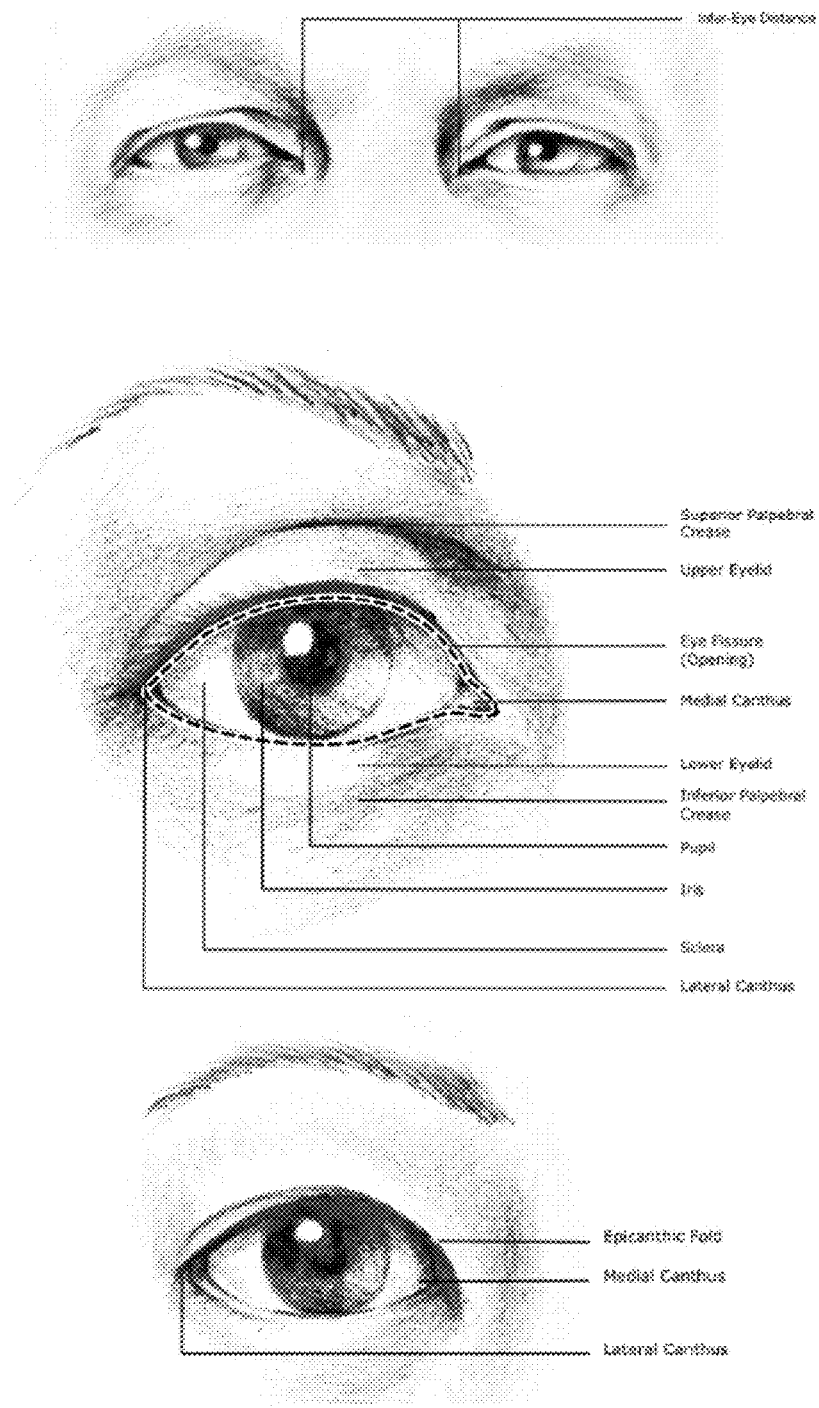
Figure 33:
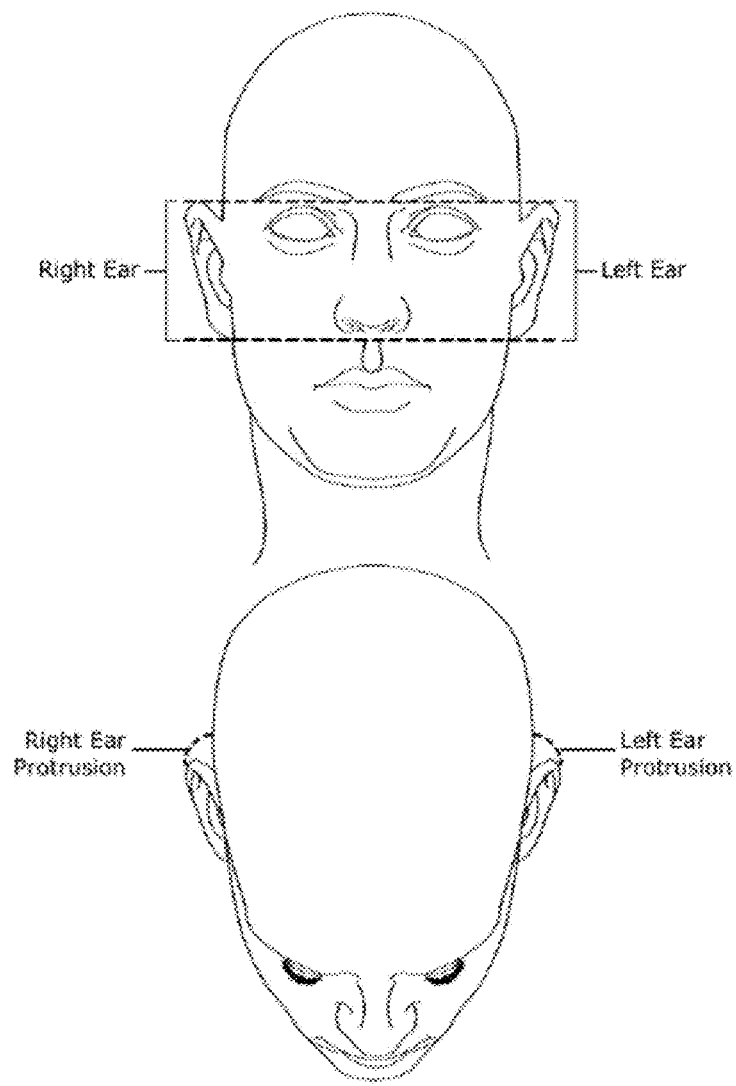
Figure 35:
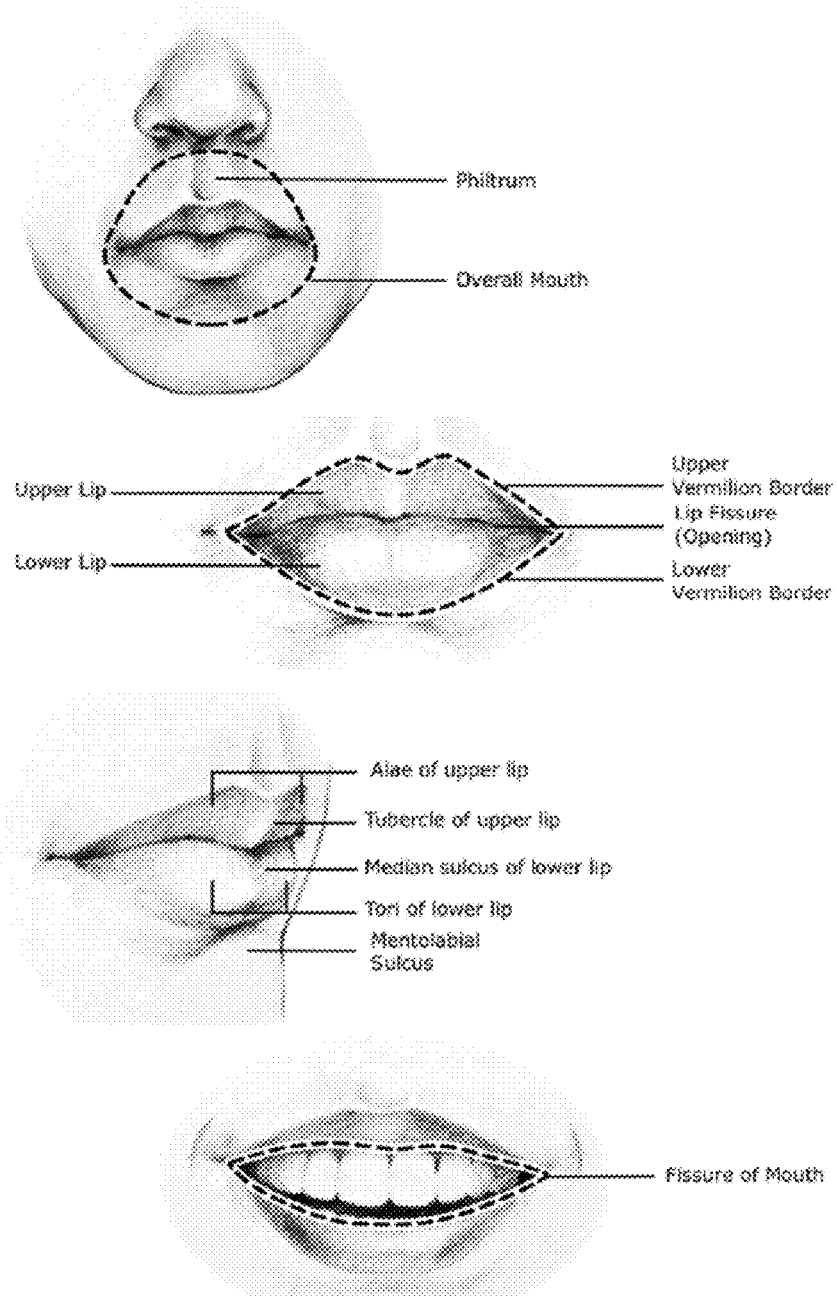
Figure 37:
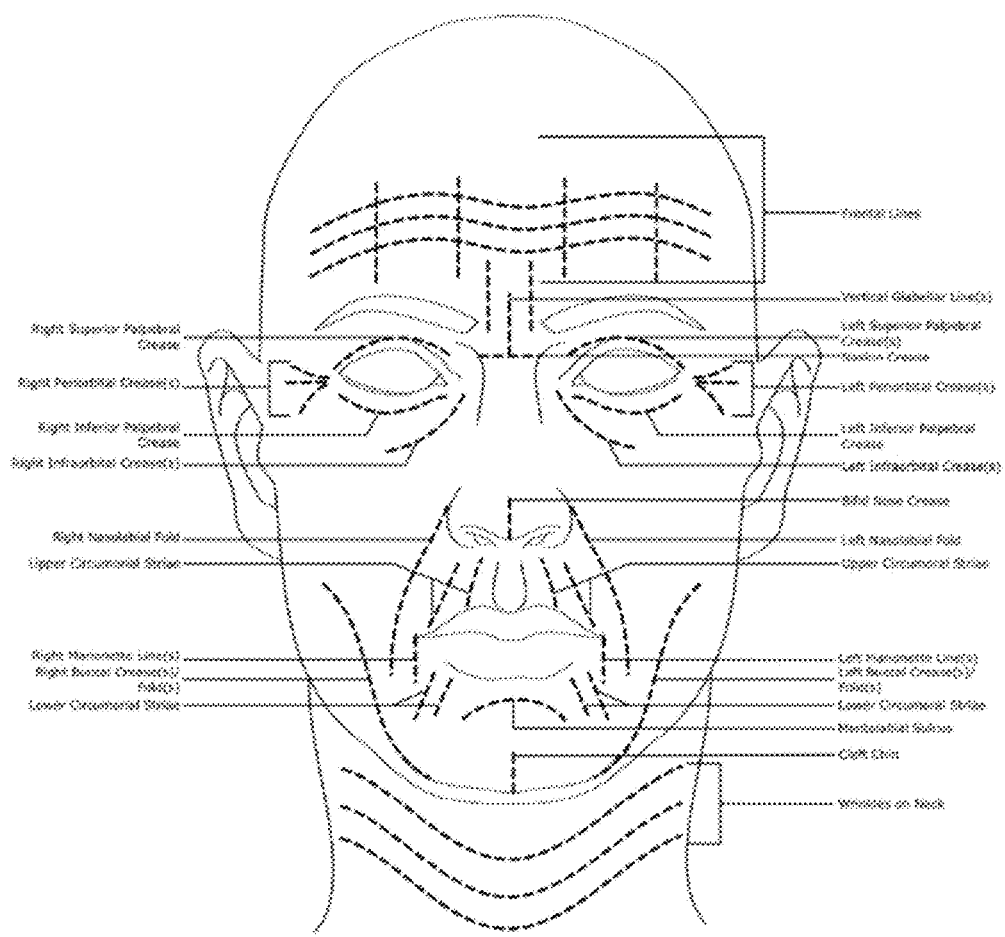

FIG. 27 outlines an exemplary method for performing facial recognition. In particular, control begins in step S2704 and continues to step S2708. In step S2708 a probe sample is loaded for display. Next, in step S2712, one or more candidate samples are loaded for display. Then, in Step S2716, the samples can be displayed in a side-by-side or other manner. Control then continues to step S2720.

In step S2720, a predefined list of facial components to be compared is maintained and managed. As discussed, an exemplary embodiment can include one or more of the following facial components that require comparisons: skin, face/head outline, face/head composition, hairline or baldness pattern, forehead, eyebrows, eyes, cheeks, nose, ears, mouth, chin or jaw line, neck, facial hair, facial lines, scars, facial marks, and alterations. Next, in step S2724, the user is guided through the examination process with reference to the predefined list. Then, in step S2728, the user is optionally provided one or more of guidelines/reference material/instructions/examples for the specific comparison being made. Optionally further, the user can have their attention drawn to a specific facial feature being compared. Optionally still, the system can automatically update the display with one or more of the guidelines/reference material/instructions/examples/drawings to correspond to the facial component currently being examined. Control then continues to step S2732.

In step S2732, the predefined list can be updated as each facial component comparison is completed. Next, in step S2736, the user can optionally be required to complete a current comparison before being allowed to proceed to a next comparison. Then, in step S2740, user actions can optionally be logged as discussed. Control then continues to step S2744.

In step S2744, the user can optionally record one or more of notes/comments/images/comparison results associated with one or more of the comparisons—with one or more of these items optionally being added to a report. Next, in step S2748, the user can optionally be required to perform all comparisons for completion of the facial identification process—with the user optionally being returned to complete any incomplete comparisons. Then, in step S2752 an audit report can optionally be generated. Control then continues to step S2756. In step S2756, a finalization report can be generated with control continuing to step S2760 where the control sequence ends.

In accordance with yet another optional embodiment, the system can include an application that can run on a desktop (e.g., Forensic Spectacles) which allows a user to control and directly push any two images currently displayed anywhere on the desktop directly into a 1:1 examination screen. This allows a user to, for example, see facial expressions—this allows "one click facial review." In another exemplary embodiment, the linked magnifiers can "snap" examination areas of interest into an off screen repository where they can then be directly published into a finalization document. This allows users to create the final examination report as part of their workflow which can, for example, dramatically shorten the time to create the final report.

In accordance with another exemplary embodiment, the checklist (predefined list) can also lay out the facial components. Another window can optionally be shown that references the correct and accepted anatomical definitions of the facial components. Both the checklist and the definitions can be synced to the facial component the examiner is currently reviewing. This can provide for each facial component 1) a checklist of what to look for, and 2) the proper anatomical terms for the specific component. Therefore, the examiner can be given a full suite of items and proper anatomical definitions for managing the facial identification. FIGS. 28-37 show examples of accepted anatomical definitions of the facial components which are available from fiswg.org—Facial Image Comparison Feature List for Morphological Analysis, which is incorporated herein by reference in its entirety.

Additionally, the following two documents, which are also incorporated herein by reference in their entirety, provide information and background: SWGFAST, Document #10, Standards for Examining Friction Ridge, Impressions and Resulting Conclusions (Latent/Tenprint) at www.swgfast.org/documents/examinations-conclusions/121124_Examinations-Conclusions_2.0.pdf and SWGFAST, Document #8, Standard for the Documentation of Analysis, Comparison, Evaluation, and Verification (ACE-V) at www.swgfast.org/documents/documentation/121124_Standard-Documentation-ACE-V_2.0.pdf.

Exemplary aspects are directed toward:

A method of performing a facial identification process, the method comprising:

displaying two facial images on a display screen adjacent to each other;

electronically maintaining a predefined list of facial components to be examined when the two facial images on the display screen are analyzed by a user to determine whether the facial images are of different persons or of a same person; and automatically guiding the user through the facial identification process in response to the electronically maintained list of facial components.

Any of the above aspects, wherein the list of facial components includes skin, face/head outline, face/head composition, hairline or baldness pattern, forehead, eyebrows, eyes, cheeks, nose, ears, mouth, chin or jaw line, neck, facial hair, facial lines, scars, facial marks, and alterations.

Any of the above aspects, further comprising requiring the user to complete examination of a facial component currently being examined before examination can proceed to another facial component in the list of facial components.

Any of the above aspects, further comprising synchronizing the display of the two facial images with a facial component currently being examined by the user.

Any of the above aspects, wherein the synchronizing the display of the two facial images with the facial component currently being examined by the user includes electronically drawing attention to the current facial component in both of the facial images.

Any of the above aspects, wherein electronically drawing attention to the current facial component in both of the facial images includes one or more of: drawing a box around the current facial component, pointing an arrow to the current facial component, correlating the facial component to pertinent reference material, magnifying the facial component being reviewed, placing the two facial components in a way which is easier for the user to compare, blurring the facial areas not being reviewed, and highlighting the current facial component with color.

Any of the above aspects, further comprising displaying the list of facial components on a display screen, while the two facial images are being displayed.

Any of the above aspects, further comprising electronically displaying one or more of a description, instructions, and drawings related to performing an examination of a facial component currently being examined by the user, while the two facial images are being displayed.

Any of the above aspects, further comprising automatically updating the display of the one or more of a description, instructions, and drawings to correspond to the facial component currently being examined.

Any of the above aspects, further comprising generating an audit record containing every facial component in the list that was examined by the user.

Any of the above aspects, further comprising requiring the user to examine every facial component in the list of facial components in order to complete the facial identification process.

Any of the above aspects, further comprising receiving input from the user that centers eye locations in each of the displayed facial images.

Any of the above aspects, further comprising maintaining a viewed status and a comparison results status for each of the facial components in the list.

Any of the above aspects, wherein the automatically guiding the user through the facial identification process includes examining the facial components in the predefined list of facial components sequentially.

Any of the above aspects, further comprising magnifying a facial component currently being examined in both of the displayed facial images.

Computer program product for performing a facial identification process, the computer program product comprising:

a non-transitory computer readable storage medium having computer readable program code embodied therewith, the computer readable program code comprising:

computer readable program code that, if executed, displays two facial images on a display screen adjacent to each other;

computer readable program code that, if executed, provides a predefined list of facial components to be examined when the two facial images on the display screen are analyzed by a user to determine whether the facial images are of different persons or of a same person;

computer readable program code that, if executed, automatically guides the user through the facial identification process based on the list of facial components.

Any of the above aspects, wherein the list of facial components includes skin, face/head outline, face/head composition, hairline or baldness pattern, forehead, eyebrows, eyes, cheeks, nose, ears, mouth, chin or jaw line, neck, facial hair, facial lines, scars, facial marks, and alterations.

Any of the above aspects, further comprising computer readable program code that, if executed, requires the user to complete examination of a facial component currently being examined before examination can proceed to another facial component in the list of facial components.

Any of the above aspects, further comprising computer readable program code that, if executed, synchronizes the display of the two facial images with a facial component currently being examined by the user.

Any of the above aspects, wherein the computer readable program code that, if executed, synchronizes the display of the two facial images with the facial component currently being examined by the user includes computer readable program code that, if executed, electronically draws attention to the current facial component in both of the facial images.

Any of the above aspects, wherein the computer readable program code that, if executed, electronically draws attention to the current facial component in both of the facial images includes computer readable program code to perform one or more of: drawing a box around the current facial component, pointing an arrow to the current facial component, correlating the facial component to pertinent reference material, magnifying the facial component being reviewed, placing the two facial components in a way which is easier for the user to compare, blurring the facial areas not being reviewed, and highlighting the current facial component with color.

Any of the above aspects, further comprising computer readable program code that, if executed, displays the list of facial components on a display screen, while the two facial images are being displayed.

Any of the above aspects, further comprising computer readable program code that, if executed, electronically displays one or more of a description, instructions, and drawings related to performing an examination of a facial component currently being examined by the user, while the two facial images are being displayed.

Any of the above aspects, further comprising computer readable program code that, if executed, automatically updates the display of the one or more of a description, instructions, and drawings to correspond to the facial component currently being examined.

Any of the above aspects, further comprising computer readable program code that, if executed, generates an audit record containing every facial component in the list that was examined by the user.

Any of the above aspects, further comprising computer readable program code that, if executed, requires the user to examine every facial component in the list of facial components in order to complete the facial identification process.

Any of the above aspects, further comprising computer readable program code that, if executed, receives input from the user that centers eye locations in each of the displayed facial images.

Any of the above aspects, further comprising computer readable program code that, if executed, maintains a viewed status and a comparison results status for each of the facial components in the list.

Any of the above aspects, wherein the computer readable program code that, if executed, automatically guides the user through the facial identification process includes computer readable program code that, if executed, sequentially examines the facial components in the predefined list of facial components.

Any of the above aspects, further comprising computer readable program code that, if executed, magnifies a facial component currently being examined in both of the displayed facial images.

A computer system of performing a facial identification process, the computer system comprising:
memory storing program code used to perform a facial identification process;
a processor executing the program code stored in the memory to:
display two facial images on a display screen adjacent to each other;
electronically maintain a predefined list of facial components to be examined when the two facial images on the display screen are analyzed by a user to determine whether the facial images are of different persons or of a same person; and
automatically guide the user through the facial identification process in response to the electronically maintained list of facial components.

Any of the above aspects, wherein the computer system is configured to perform any of the above aspects.

A facial identification system to automatically assist with performing a facial identification process comprising:
an I/O interface in communication with one or more biometric systems and databases, the I/O interface receiving image information including facial images;
at least one display and graphics processing unit in communication that cooperate to display at least two facial images near one other;
a processor and storage in electrical communication that electronically maintain a predefined list of facial components to be examined when the two facial images on the at least one display are analyzed by a user to determine whether the facial images are of different persons or of a same person;
a guideline database; and
a facial component list manager that automatically guides the user through the facial identification process in response to the electronically maintained list of facial components, wherein the automatic guiding includes providing one or more of instructions, guidelines and anatomical definitions from the guideline database to the user and keeping track of which facial components have been examined.

Any of the above aspects, wherein the facial images are managed in one or more folders including a sent folder, an inbox folder and a reviewed folder.

A system for performing a facial identification process comprising:
means for displaying two facial images on a display screen adjacent to each other;
means for electronically maintaining a predefined list of facial components to be examined when the two facial images on the display screen are analyzed by a user to determine whether the facial images are of different persons or of a same person; and
means for automatically guiding the user through the facial identification process in response to the electronically maintained list of facial components.

One or more means for performing any one or more of the above functions.

Any one or more of the features as substantially described herein.

For purposes of explanation, numerous details are set forth in order to provide a thorough understanding of the present embodiments. It should be appreciated however that the techniques herein may be practiced in a variety of ways beyond the specific details set forth herein.

Furthermore, while the exemplary embodiments illustrated herein may show the various components of the system collocated, it is to be appreciated that the various components of the system can be located at distant portions of a distributed network, such as a communications network and/or the Internet, or within a dedicated secure, unsecured and/or encrypted system. Thus, it should be appreciated that the components of the system can be combined into one or more devices, or collocated on a particular node/element(s) of a distributed network, such as a communications network. As will be appreciated from the description, and for reasons of computational efficiency, the components of the system can be arranged at any location within a distributed network without affecting the operation of the system.

Furthermore, it should be appreciated that the various links, including communications channel(s), connecting the elements (which may not be not shown) can be wired or wireless links, or any combination thereof, or any other known or later developed element(s) that is capable of supplying and/or communicating data and/or signals to and from the connected elements. The term module as used herein can refer to any known or later developed hardware, software, firmware, or combination thereof that is capable of performing the functionality associated with that element. The terms determine, calculate and compute, and variations thereof, as used herein are used interchangeably and include any type of methodology, process, mathematical operation or technique.

While the above-described flowcharts/operational flows have been discussed in relation to a particular exemplary sequence of events, it should be appreciated that changes to this sequence can occur without materially effecting the operation of the embodiment(s). Additionally, the exact sequence of events need not occur as set forth in the exemplary embodiments, but rather the steps can be performed by one or the other device(s) in the system. Additionally, the exemplary techniques illustrated herein are not limited to the specifically illustrated embodiments but can also be utilized with the other exemplary embodiments and each described feature is individually and separately claimable.

As will be appreciated by one skilled in the art, aspects of the present disclosure may be embodied as a system, method, and/or computer program product. Thus, aspects of the present disclosure may be embodied entirely in hardware, entirely in software (including, but not limited to, firmware, program code, resident software, microcode), or in a combination of hardware and software. All such embodiments may generally be referred to herein as a circuit, a module, or a system. In addition, aspects of the present invention may be in the form of a computer program product embodied in one or more computer readable media having computer readable program code embodied thereon.

The computer readable medium may be a computer readable storage medium, examples of which include, but are not limited to, an electronic, magnetic, optical, electromagnetic, infrared, or semiconductor system, apparatus, or device, or any suitable combination thereof. As used herein, a computer readable storage medium may be any non-transitory, tangible medium that can contain or store a program for use by or in connection with an instruction execution system, apparatus, device, computer, computing system, computer system, or any programmable machine or device that inputs, processes, and outputs instructions, commands, or data. A non-exhaustive list of specific examples of a computer readable storage medium include an electrical connection having one or more wires, a portable computer diskette, a floppy disk, a hard disk, a random access memory (RAM), a read-only memory (ROM), a USB flash drive, an non-volatile RAM (NVRAM or NOVRAM), an erasable programmable read-only memory (EPROM or Flash memory), a flash memory card, an electrically erasable programmable read-only memory (EEPROM), an optical fiber, a portable compact disc read-only memory (CD-ROM), a DVD-ROM, an optical storage device, a magnetic storage device, or any suitable combination thereof. A computer readable storage medium can be any computer readable medium that is not a computer readable signal medium such as a propagated data signal with computer readable program code embodied therein.

Program code may be embodied as computer-readable instructions stored on or in a computer readable storage medium as, for example, source code, object code, interpretive code, executable code, or combinations thereof. Any standard or proprietary, programming or interpretive language can be used to produce the computer-executable instructions. Examples of such languages include C, C++, C#, Pascal, JAVA, JAVA Script, BASIC, Smalltalk, Visual Basic, and Visual C++.

Transmission of program code embodied on a computer readable medium can occur using any appropriate medium including, but not limited to, wireless, wired, optical fiber cable, radio frequency (RF), or any suitable combination thereof.

The program code may execute entirely on a user's computer, partly on the user's computer, as a stand-alone software package, partly on the user's computer and partly on a remote computer or entirely on a remote computer or server. Any such remote computer may be connected to the user's computer through any type of network, including a local area network (LAN) or a wide area network (WAN), or the connection may be made to an external computer (for example, through the Internet using an Internet Service Provider).

Additionally, the systems, methods and protocols can be implemented to improve one or more of a special purpose computer, a programmed microprocessor or microcontroller and peripheral integrated circuit element(s), an ASIC or other integrated circuit, a digital signal processor, a hardwired electronic or logic circuit such as discrete element circuit, a programmable logic device such as PLD, PLA, FPGA, PAL, any comparable means, or the like. In general, any device capable of implementing a state machine that is in turn capable of implementing the methodology illustrated herein can benefit from the various communication methods, protocols and techniques according to the disclosure provided herein.

Examples of the processors as described herein may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARIV1926EJS™ processors, Broadcom® AirForce BCM4704/BCM4703 wireless networking processors, the AR7100 Wireless Network Processing Unit, other industry-equivalent processors, and may perform computational functions using any known or future-developed standard, instruction set, libraries, and/or architecture.

Furthermore, the disclosed methods may be readily implemented in software using object or object-oriented software development environments that provide portable source code that can be used on a variety of computer, workstation or mobile device platforms. Alternatively, the disclosed system may be implemented partially in hardware using standard logic circuits or a VLSI design. Whether software or hardware is used to implement the systems in accordance with this invention is dependent on the speed and/or efficiency requirements of the system, the particular function, and the particular software or hardware systems or microprocessor or microcomputer systems being utilized. The methods illustrated herein however can be readily implemented in hardware and/or software using any known or later developed systems or structures, devices and/or software by those of ordinary skill in the applicable art from the functional description provided herein and with a general basic knowledge of the computer and image processing arts.

Moreover, the disclosed methods may be readily implemented in software executed on programmed general-purpose computer, a special purpose computer, mobile device, smartphone, a microprocessor, or the like. In these instances, the systems and methods of this invention can be implemented as program embedded on personal computer such as JAVA® or CGI script, as a resource residing on a server or graphics workstation, as a routine embedded in a dedicated fingerprint processing system, as a plug-in, or the like. The system can also be implemented by physically incorporating the system and method into a software and/or hardware system, such as the hardware and software systems of an image processor.

While this invention has been described in conjunction with a number of embodiments, it is evident that many alternatives, modifications and variations would be or are apparent to those of ordinary skill in the applicable arts. Accordingly, it is intended to embrace all such alternatives, modifications, equivalents, and variations that are within the spirit and scope of this invention.

The invention claimed is:

1. A method of providing electronically assisted facial identification comprising:
   displaying, on at least one display for a human facial examiner, at least two facial images;
   electronically maintaining, by a processor and storage, a predefined list of facial components to be examined by the human facial examiner in the least two facial images, the predefined list of facial components guiding the human facial examiner to assist the human facial examiner with determining whether the facial images are of different persons or of a same person; and automatically guiding the human facial examiner through the facial identification process in response to interaction with the electronically maintained list of facial components, wherein the automatic guiding includes providing one or more of instructions, guidelines and anatomical definitions to the human facial examiner, and maintaining in storage an electronic database of which facial components have been examined.

2. The method of claim 1, wherein the list of facial components includes one or more of: skin, face/head outline, face/head composition, hairline or baldness pattern, forehead, eyebrows, eyes, cheeks, nose, ears, mouth, chin or jaw line, neck, facial hair, facial lines, scars, facial marks, and alterations.

3. The method of claim 1, further comprising requiring the human facial examiner to complete examination of a facial component currently being examined before examination can proceed to another facial component in the list of facial components.

4. The method of claim 1, further comprising automatically synchronizing the display of the two facial images with a facial component currently being examined by the human facial examiner.

5. The method of claim 4, wherein the synchronizing the display of the two facial images with the facial component currently being examined by the human facial examiner includes automatically electronically drawing attention to the current facial component in both of the facial images.

6. The method of claim 5, wherein electronically drawing attention to the current facial component in both of the facial images includes one or more of: drawing a box around the current facial component, pointing an arrow to the current facial component, correlating the facial component to pertinent reference material, magnifying the facial component being reviewed, placing the two facial components in a way which is easier for the human facial examiner to compare the components, blurring the facial areas not being reviewed, and highlighting the current facial component with color.

7. The method of claim 1, further comprising displaying the list of facial components on the display screen, while the two facial images are being displayed.

8. The method of claim 1, further comprising automatically and dynamically electronically displaying one or more of a description, the instructions, and drawings related to performing an examination of a facial component currently being examined by the human facial examiner, while the two facial images are being displayed.

9. The method of claim 8, further comprising automatically updating the display of the one or more of a description, instructions, and drawings to correspond to the facial component currently being examined.

10. The method of claim 1, further comprising generating an audit record containing every facial component in the list that was examined by the human facial examiner.

11. The method of claim 1, further comprising requiring the human facial examiner to examine every facial component in the list of facial components in order to complete the facial identification process.

12. The method of claim 1, further comprising receiving input from the human facial examiner that centers eye locations in each of the displayed facial images.

13. The method of claim 1, further comprising maintaining a viewed status and a comparison results status for each of the facial components in the list.

14. The method of claim 1, wherein the automatically guiding the human facial examiner through the facial identification process includes examining the facial components in the predefined list of facial components sequentially.

15. The method of claim 1, further comprising magnifying a facial component currently being examined in both of the displayed facial images.

16. A facial identification system to automatically assist with performing a facial identification process comprising:
at least one display and graphics processing unit that cooperate to display at least two facial images near one other;
a processor and storage in electrical communication that electronically maintain a predefined list of facial components to be examined when the two facial images on the at least one display are analyzed by a human facial examiner to determine whether the facial images are of different persons or of a same person; and
a facial component list manager that automatically guides the human facial examiner through the facial identification process in response to the electronically maintained list of facial components, wherein the automatic guiding includes providing one or more of instructions, guidelines and anatomical definitions to the human facial examiner and keeping track of which facial components have been examined by the human facial examiner.

17. The system of claim 16, wherein the list of facial components includes one or more of: skin, face/head outline, face/head composition, hairline or baldness pattern, forehead, eyebrows, eyes, cheeks, nose, ears, mouth, chin or jaw line, neck, facial hair, facial lines, scars, facial marks, and alterations.

18. The system of claim 16, further comprising a facial component auditor that requires the human facial examiner to complete examination of a facial component currently being examined before examination can proceed to another facial component in the list of facial components.

19. The system of claim 16, wherein the graphics processing unit automatically synchronizes the display of the two facial images with a facial component currently being examined by the human facial examiner.

20. The system of claim 19, wherein the synchronizing the display of the two facial images with the facial component currently being examined by the human facial examiner includes automatically electronically drawing attention to the current facial component in both of the facial images.

21. The system of claim 20, wherein electronically drawing attention to the current facial component in both of the facial images includes one or more of: drawing a box around the current facial component, pointing an arrow to the current facial component, correlating the facial component to pertinent reference material, magnifying the facial component being reviewed, placing the two facial components in a way which is easier for the human facial examiner to compare, blurring the facial areas not being reviewed, and highlighting the current facial component with color.

22. The system of claim 16, wherein the facial component list manager displays the list of facial components on a display screen, while the two facial images are being displayed.

23. The system of claim 16, further comprising automatically and dynamically electronically displaying one or more of a description, the instructions, and drawings related to performing an examination of a facial component currently being examined by the human facial examiner, while the two facial images are being displayed.

24. The system of claim 23, further comprising a facial component verifier that automatically updates the display of the one or more of a description, instructions, and drawings to correspond to the facial component currently being examined.

25. The system of claim 16, further comprising an audit report module in electrical communication with the processor to generate an audit record containing every facial component in the list that was examined by the human facial examiner.

26. The system of claim 16, further comprising a facial component auditor that requires the human facial examiner to examine every facial component in the list of facial components in order to complete the facial identification process.

27. The system of claim 16, further comprising an I/O device that receives input from the human facial examiner that centers eye locations in each of the displayed facial images.

28. The system of claim 16, further comprising a facial component auditor that maintains in the storage a viewed status and a comparison results status for each of the facial components in the list.

29. The system of claim 16, wherein the automatically guiding the human facial examiner through the facial identification process includes examining the facial components in the predefined list of facial components sequentially.

30. The system of claim 16, further comprising a magnifier module that magnifies a facial component currently being examined in both of the displayed facial images.

* * * * *